(12) United States Patent
Nagai et al.

(10) Patent No.: US 9,958,265 B2
(45) Date of Patent: May 1, 2018

(54) SPECIMEN MEASURING DEVICE AND COMPUTER PROGRAM PRODUCT

(71) Applicants: Sho Nagai, Kanagawa (JP); Kensuke Masuda, Kanagawa (JP); Go Maruyama, Kanagawa (JP); Yuji Yamanaka, Tokyo (JP); Naohiro Kamijo, Kanagawa (JP); Kenji Kagitani, Kanagawa (JP)

(72) Inventors: Sho Nagai, Kanagawa (JP); Kensuke Masuda, Kanagawa (JP); Go Maruyama, Kanagawa (JP); Yuji Yamanaka, Tokyo (JP); Naohiro Kamijo, Kanagawa (JP); Kenji Kagitani, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 287 days.

(21) Appl. No.: 14/816,374

(22) Filed: Aug. 3, 2015

(65) Prior Publication Data
US 2016/0040985 A1      Feb. 11, 2016

(30) Foreign Application Priority Data

Aug. 5, 2014 (JP) ................. 2014-159917

(51) Int. Cl.
 *G01J 3/28* (2006.01)
 *G01B 11/30* (2006.01)
 (Continued)

(52) U.S. Cl.
 CPC .......... *G01B 11/306* (2013.01); *G01B 11/303* (2013.01); *G01J 3/14* (2013.01);
 (Continued)

(58) Field of Classification Search
 CPC ...... G01B 11/30; G01N 21/251; G01N 21/51; G01N 2021/8427; G06T 15/506
 See application file for complete search history.

(56) References Cited

U.S. PATENT DOCUMENTS

| 7,391,518 B1 * | 6/2008 | Schwarz ................ G01B 11/30 356/445 |
| 7,679,747 B2 * | 3/2010 | Kuwada ................. G01N 21/57 356/445 |

(Continued)

FOREIGN PATENT DOCUMENTS

| JP | 2004-20263 A | 1/2004 |
| JP | 2009-128083 A | 6/2009 |

(Continued)

OTHER PUBLICATIONS

Extended European Search Report dated Jan. 27, 2016 in Patent Application No. 15179645.5.
Office Action dated Mar. 24, 2017 in European Patent Application No. 15 179 645.5.

*Primary Examiner* — Kara E Geisel
*Assistant Examiner* — Maurice Smith
(74) *Attorney, Agent, or Firm* — Oblon, McClelland, Maier & Neustadt, L.L.P.

(57) ABSTRACT

A specimen measuring device includes: a light source device that irradiates a specimen surface of a specimen with illumination light from multiple illumination units at a plurality of illumination angles; a spectral camera device that is arranged above the specimen surface, spectrally separates reflected light from the specimen surface, and acquires 2D spectral information through a single image capturing operation; and a calculating unit that calculates deflection angle spectral information of the specimen surface used to measure a measurement value of a certain evaluation item of the specimen using a change in an optical geometrical condition (Continued)

of an illumination direction and an image capturing direction between pixels in an X axis direction and a Y axis direction of the spectral information.

14 Claims, 27 Drawing Sheets

(51) Int. Cl.
| | |
|---|---|
| *G01J 3/18* | (2006.01) |
| *G01J 3/14* | (2006.01) |
| *G01N 21/25* | (2006.01) |
| *G01N 21/55* | (2014.01) |
| *G01N 21/84* | (2006.01) |
| *G01J 3/51* | (2006.01) |
| *G01J 3/50* | (2006.01) |
| *G01N 21/47* | (2006.01) |
| *G01N 21/57* | (2006.01) |
| *G01N 21/17* | (2006.01) |
| *G01N 21/31* | (2006.01) |

(52) U.S. Cl.
CPC .............. *G01J 3/18* (2013.01); *G01N 21/251* (2013.01); *G01N 21/255* (2013.01); *G01N 21/55* (2013.01); *G01N 21/8422* (2013.01); *G01J 3/504* (2013.01); *G01J 3/513* (2013.01); *G01N 21/4738* (2013.01); *G01N 21/4785* (2013.01); *G01N 21/57* (2013.01); *G01N 2021/1776* (2013.01); *G01N 2021/3177* (2013.01); *G01N 2021/4711* (2013.01); *G01N 2021/575* (2013.01); *G01N 2201/0635* (2013.01)

(56) References Cited

U.S. PATENT DOCUMENTS

| | | | |
|---|---|---|---|
| 7,991,596 B2 * | 8/2011 | Steenhoek | G01N 21/4738 356/405 |
| 2002/0167669 A1 * | 11/2002 | Schwarz | G01N 21/474 356/446 |
| 2004/0197020 A1 | 10/2004 | Sones | |
| 2006/0245632 A1 * | 11/2006 | Nisper | G01J 3/02 382/135 |
| 2006/0274316 A1 * | 12/2006 | Perquis | G01J 3/46 356/446 |
| 2007/0097119 A1 * | 5/2007 | Steenhoek | C09D 5/36 345/426 |
| 2009/0213120 A1 * | 8/2009 | Nisper | G01J 3/504 345/426 |
| 2012/0032973 A1 * | 2/2012 | Sano | G01J 3/504 345/593 |
| 2014/0078379 A1 * | 3/2014 | Masuda | H04N 9/045 348/360 |
| 2014/0152990 A1 * | 6/2014 | Ehbets | G01J 3/50 356/405 |
| 2014/0192255 A1 * | 7/2014 | Shroff | G01N 21/27 348/362 |
| 2014/0242271 A1 * | 8/2014 | Prakash | B60S 5/00 427/140 |
| 2014/0375994 A1 | 12/2014 | Yamanaka et al. | |
| 2015/0012226 A1 * | 1/2015 | Skaff | G01N 21/55 702/22 |
| 2015/0131090 A1 | 5/2015 | Osumi | |

FOREIGN PATENT DOCUMENTS

| | | |
|---|---|---|
| JP | 2013-238576 | 11/2013 |
| JP | 2015-132594 A | 7/2015 |

\* cited by examiner (DEPENDENCE OF SPECTRAL TRANSMITTANCE OF COLOR FILTER ON INCIDENT ANGLE)

DIAGRAM OF LENS ARRAY VIEWED IN OPTICAL AXIS DIRECTION

ENLARGED VIEW OF MICRO PIXEL (EXAMPLE OF COLOR CHECKER)

(24 COLORS OF COLOR CHECKER PLOTTED IN xy
CHROMATICITY DIAGRAM)

FIG.14

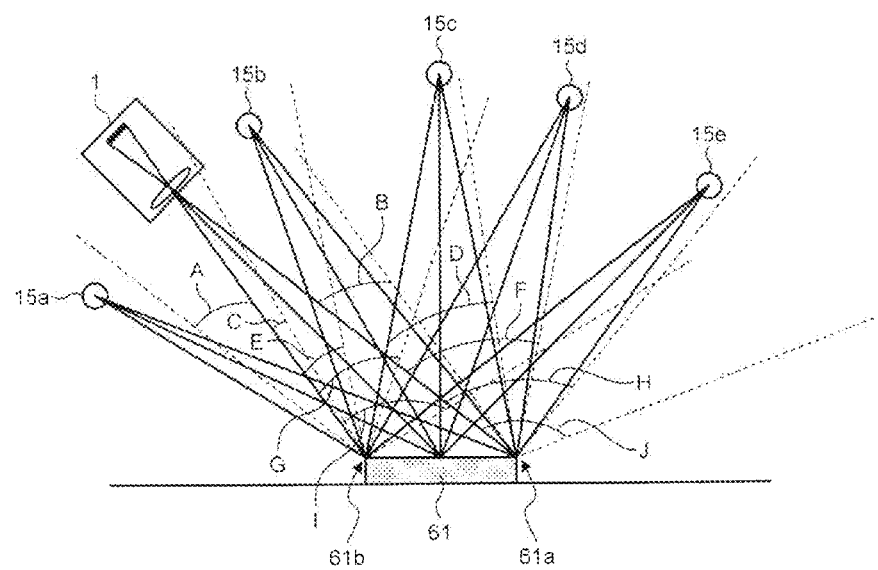

FIG.15

| ILLUMINATION UNIT | FIRST ILLUMINATION UNIT | SECOND ILLUMINATION UNIT | THIRD ILLUMINATION UNIT | FOURTH ILLUMINATION UNIT | FIFTH ILLUMINATION UNIT |
|---|---|---|---|---|---|
| ANGLE OF SPECTRAL CAMERA DEVICE | 45 | 45 | 45 | 45 | 45 |
| ANGLE OF ILLUMINATION UNIT | 65 | 35 | 0 | -20 | -45 |
| ASPECULAR ANGLE (CENTER) | 110 | 80 | 45 | 25 | 0 |
| LEFT END ANGLE OF SPECIMEN | ANGLE I | ANGLE G | ANGLE E | ANGLE C | ANGLE A |
| ASPECULAR ANGLE (SPECIMEN LEFT END) | 95 | 60 | 24 | 6 | -16 |
| RIGHT END ANGLE OF SPECIMEN | ANGLE J | ANGLE H | ANGLE F | ANGLE D | ANGLE B |
| ASPECULAR ANGLE (SPECIMEN RIGHT END) | 121 | 95 | 63 | 43 | 16 |

MEASUREMENT SPECIMEN LEFT END ASPECULAR ANGLE 6°

CENTER ASPECULAR ANGLE 25°

MEASUREMENT SPECIMEN RIGHT END ASPECULAR ANGLE 43°

FIG.22

7.5 *CIE 1976 Uniform Color Spaces*—When a color space more nearly uniform than $X$, $Y$, $Z$ is desired, use CIELAB or CIELUV.

7.5.1 *CIELAB or L\*a\*b\**—This approximately uniform color space is produced by plotting in rectangular coordinates the quantities $L^*$, $a^*$, $b^*$ defined as follows (3):

$$L^* = 116 f(Q_Y) - 16$$
$$a^* = 500 [f(Q_X) - f(Q_Y)]$$
$$b^* = 200 [f(Q_Y) - f(Q_Z)]$$

where:

$$Q_X = (X/X_n); Q_Y = (Y/Y_n); Q_Z = (Z/Z_n)$$

and $$f(Q_i) = Q_i^{1/3} \text{ if } Q_i > (6/29)^3$$

else $$f(Q_i) = (841/108) Q_i + 4/29 \text{ if } Q_i \leq (6/29)^3$$

where

*i varies as X, Y, and Z.*

FIG.23

7.5.2 *CIELUV* or *L\*u\*v\**—This approximately uniform color space is produced by plotting in rectangular coordinates the quantities $L^*$, $u^*$, $v^*$ defined as follows (see also Note 5):

$$L^* = 116(Y/Y_n)^{1/3} - 16 \qquad Y/Y_n > (6/29)^3$$

$$u^* = 13L^*(u' - u'_n)$$

$$v^* = 13L^*(v' - v'_n)$$

with:

$$u' = \frac{4X}{X + 15Y + 3Z}$$

$$v' = \frac{9Y}{X + 15Y + 3Z}$$

$$u'_n = \frac{4X_n}{X_n + 15Y_n + 3Z_n}$$

$$v'_n = \frac{9Y_n}{X_n + 15Y_n + 3Z_n}$$

FIG.30

11.2 For Test Method B, calculate the mean of three readings of each specimen for:
 11.2.1 Specular gloss, $R_{s,20}$ at 20°.
 11.2.2 One or more of the following, as required:
 11.2.2.1 Reflection haze, $H_{20}$.
 11.2.2.2 Logarithmic reflection haze, $H_{20,\log} = 1285 \log[(H_{20}/20) + 1]$.
 11.2.2.3 Compensated reflection haze, $H_{20,\text{comp}} = H_{20,\text{specimen}} - (H_{20,n} \times Y_{\text{specimen}}/Y_n)$.

NOTE 4—$H_{20,\log}$ may also be calculated as a compensated quantity by using $H_{20,\text{comp}}$ in place of $H_{20}$ in 11.2.2.2. Compensated quantities shall be used when comparing specimens with different values of $Y$.

FIG.31

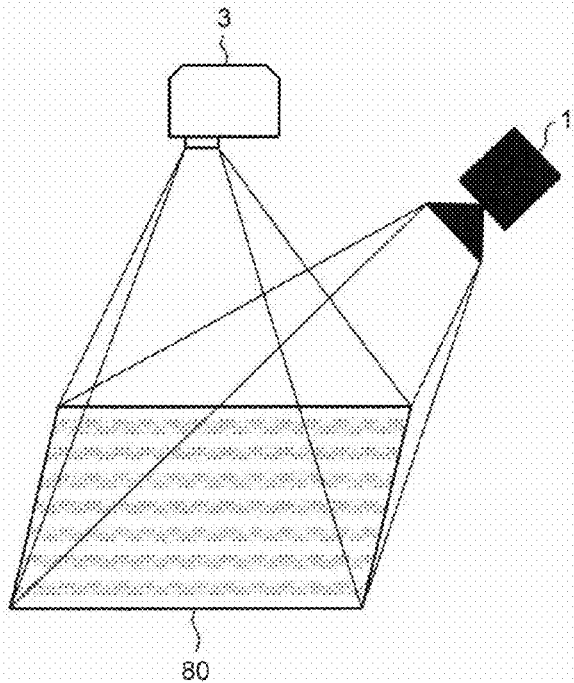

SPECIMEN MEASURING DEVICE AND COMPUTER PROGRAM PRODUCT

CROSS-REFERENCE TO RELATED APPLICATIONS

The present application claims priority to and incorporates by reference the entire contents of Japanese Patent Application No. 2014-159917 filed in Japan on Aug. 5, 2014.

BACKGROUND OF THE INVENTION

1. Field of the Invention

The present invention relates to a specimen measuring device and a computer program product.

2. Description of the Related Art

In these days, as an evaluation of a paint including a glittering material that looks a different color according to an observation angle such as a pearlescent color or a metallic color, a multi-angle color measuring method defined in an ASTM standard (E2539-12) has been known. ASTM stands for American Society for Testing and Materials. In the case of the color measuring method defined in the ASTM standard, however, there was a problem in that a color measurement result is not identical to an evaluation by visual observation.

Japanese Patent Application Laid-open No. 2013-238576 discloses a variable angle spectral imaging measurement device that is high in accuracy and practicality. The variable angle spectral imaging measurement device includes an illumination device that irradiates a measurement sample surface with illumination light in two or more angle directions, an image forming optical lens, and a black and white two-dimensional (2D) image sensor. Variable angle spectral imaging information is measured using a change in an optical geometrical condition between pixels in X axis and Y axis directions in an image. As a result, it is possible to measure variable angle information and spectral information of each pixel accurately in a short time for all pixels of a 2D image. Thus, it is possible to implement the variable angle spectral imaging measurement device that is high in accuracy and practicality.

Here, as evaluation items of a paint including a glittering material that looks a different color according to an observation angle, evaluation items of a "glittering feeling" and a "graininess" expressed based on a distribution of a glittering material such as an interference material have been known. Further, as evaluation items of a paint including a glittering material that looks a different color according to an observation angle, evaluation items of "orange peel" and "image clarity" indicating a luster and a gloss of a paint surface state have been known.

However, in the multi-angle color measuring method defined in the ASTM standard (E2539-12), it is difficult to quantify the texture such as the glittering feeling, the graininess, the orange peel, and the image clarity in a paint including a glittering material that looks a different color according to an observation angle. For this reason, in the past, the texture such as the glittering feeling, the graininess, the orange peel, and the image clarity was often evaluated by visual observation. Further, in the multi-angle color measuring method defined in the ASTM standard (E2539-12), since it was difficult to quantify the texture such as the glittering feeling, there was a problem in that it was difficult to quantify the quality of a paint including a glittering material that looks a different color according to an observation angle comprehensively.

In light of the above, there is a need to provide a specimen measuring device and a computer program product with which the quality of various paints can be quantified comprehensively.

SUMMARY OF THE INVENTION

It is an object of the present invention to at least partially solve the problems in the conventional technology.

A specimen measuring device includes: a light source device that irradiates a specimen surface of a specimen with illumination light from multiple illumination units at a plurality of illumination angles; a spectral camera device that is arranged above the specimen surface, spectrally separates reflected light from the specimen surface, and acquires 2D spectral information through a single image capturing operation; and a calculating unit that calculates deflection angle spectral information of the specimen surface used to measure a measurement value of a certain evaluation item of the specimen using a change in an optical geometrical condition of an illumination direction and an image capturing direction between pixels in an X axis direction and a Y axis direction of the spectral information.

A computer program product includes a non-transitory computer-readable medium containing an information processing program. The program causes a computer to function as: a light source control unit that controls a light source device such that a specimen surface of a specimen is irradiated with illumination light from multiple illumination units at a plurality of illumination angles; an image capturing control unit that controls a spectral camera device arranged above the specimen surface such that reflected light from the specimen surface is spectrally separated to acquire 2D spectral information through a single image capturing operation; and a calculating unit that calculates deflection angle spectral information of the specimen surface used to measure a measurement value of a certain evaluation item of the specimen using a change in an optical geometrical condition of an illumination direction and an image capturing direction between pixels in an X axis direction and a Y axis direction of the spectral information.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 14 is a diagram illustrating a positional relation of a spectral camera device and illumination units of a light source device in the specimen measuring device according to the first embodiment;

FIG. 15 is a diagram illustrating angles formed by a positional relation of a spectral camera device and illumination units of a light source device in the specimen measuring device according to the first embodiment;

FIG. 22 is a diagram illustrating an example of an operational expression of deflection angle color measurement information;

FIG. 23 is a diagram illustrating another example of an operational expression of deflection angle color measurement information;

FIG. 30 is a diagram illustrating an example of an operational expression used for a calculation of a measurement value of a haze;

FIG. 31 is a diagram illustrating slit light of a certain wavelength projected when measurement values of image clarity and orange peel are calculated;

DETAILED DESCRIPTION OF THE PREFERRED EMBODIMENTS

Figure 1:
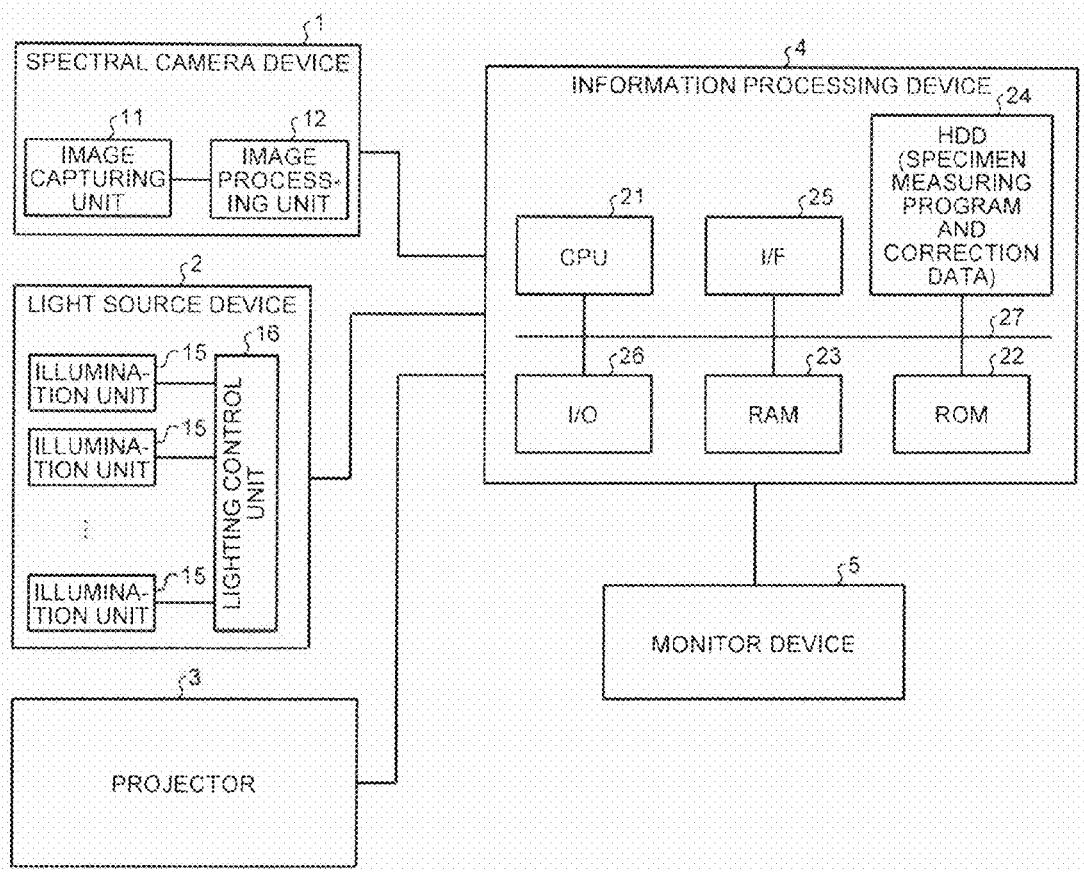
FIG. 1 is a block diagram of a specimen measuring device according to a first embodiment.

Hereinafter, embodiments of a specimen measuring device to which the present invention is applied will be described in detail with reference to the appended drawings.

Overview First, a specimen measuring device according to an embodiment can acquire deflection angle spectral information, deflection angle color measurement information, and bidirectional reflectance distribution function (BRDF) information through the following optical configuration. The BRDF information is a function specific to a reflection point which indicates a quantity of light reflected in each direction when light is incident on a certain reflection point in a certain direction. The BRDF information uses spectral information of wavelengths of light of three types of red (R), green (G), and blue (B).

Specifically, spectral information is acquired from reflected light by irradiating a specimen with an illumination at two or more angles installed in a range designated by a calculation formula and image capturing by a single image capturing operation (one shot) using a 2D spectral camera. Further, the deflection angle spectral information is obtained using a change of an optical geometrical condition of an illumination direction and an image capturing direction between pixels in an X axis direction and a Y axis direction in a 2D image from which 2D spectral information of a specimen is obtained. As a result, it is possible to regard an in-plane of the 2D image as a uniform specimen and obtain the deflection angle spectral information, the deflection angle color measurement information, and the BRDF information of an angle range determined as a measurement range.

Next, the specimen measuring device according to the embodiment digitizes the texture such as the glittering feeling, the graininess, the gloss, and the haze (turbidity (opacity)), the image clarity, and the orange peel using the following measurement method. The orange peel refers to a phenomenon of spot unevenness caused by scattered reflection of light arising from a material of a display material (a phenomenon that looks like a fizz of an incomplete wave).

1. The "glittering feeling" is digitized as follows. In other words, a spectral camera has an optical configuration in which a resolution of one pixel on a specimen is, for example, 10 μm to 100 μm, and performs image capturing in a dynamic range of 18 bits or more using a high dynamic range technique. Further, a brightness histogram of each spectral wavelength is calculated for each illumination angle, and a glittering area and glittering strength of each angle and each wavelength are calculated.

2. The graininess is digitized as follows. In other words, an image is reconstructed through the spectral camera of the above-mentioned resolution using only pixels determined as diffusion light that has avoided regular-reflected light of an illumination in a particle image of each illumination angle. Further, uniformity of a bright/dark area is digitized from a reconstructed image as the graininess. The uniformity may be obtained using entropy or variance of an image or may be obtained by Fourier analysis.

3. The gloss is digitized using spectral information of approximately 555 nm serving as human visibility and a correction result on the standard glass plate in pixels in which an image of regular-reflected light is captured.

4. The haze (turbidity (opacity)) is digitized using spectral information of approximately 555 nm serving as human visibility and a correction result on the standard glass plate for a specimen surface deviated from regular-reflected light and regular-reflected light by 1.9° to 3°.

5. The image clarity is digitized using spectral information of approximately 555 nm serving as human visibility and a correction result on the standard glass plate by capturing an image of slit light (light of a slit pattern) having a short wavelength projected from a projector through the spectral camera.

6. The orange peel is digitized using spectral information of approximately 555 nm serving as human visibility and a correction result on the standard glass plate by capturing an image of slit light having a short wavelength projected from a projector through the spectral camera.

Further, the specimen measuring device according to the embodiment acquires a three-dimensional (3D) shape of a specimen using slit light projected from a projector. Alternatively, the specimen measuring device according to the embodiment acquires a 3D shape of a specimen through a 3D acquisition device. Further, the specimen measuring device according to the embodiment corrects the deflection angle spectral information in a normal line direction of the acquired 3D shape of the specimen. Thus, it is possible to measure a specimen without being influenced by the shape of a measurement target surface.

As described above, the specimen measuring device according to the embodiment acquires the deflection angle spectral information, the deflection angle color measurement information, and the BRDF information, and digitizes the texture of a paint such as the glittering feeling, the graininess, the gloss, the haze, the image clarity, and the orange peel. Thus, it is possible to perform a quantitative evaluation on a paint including a glittering material that looks a different color according to an observation angle such as a pearlescent color or a metallic at a time.

First Embodiment

FIG. 1 is a block diagram illustrating a specimen measuring device according to a first embodiment. The specimen measuring device includes a spectral camera device 1, a light source device 2, a projector 3, an information processing device 4, and a monitor device 5 as illustrated in FIG. 1.

As will be described later, a multi-band camera device may be used as the spectral camera device 1. The multi-band camera device acquires spectral information according to the number of spectral filters for each micro lens through a spectral filter group inserted into a main lens and a micro lens array inserted between the main lens and the light receiving element as a spectral information acquiring unit that acquires 2D spectral information. Further, a hyper spectral camera device including one or more sets of filters and diffraction gratings (or prisms) may be used as the spectral camera device 1.

The spectral camera device 1 includes an image capturing unit 11 and an image processing unit 12, and acquires 2D spectral information through a single image capturing operation (one shot) in synchronization with emission of light from illumination units 15 of the light source device 2 which are fixed at respective angles. For example, the single image capturing operation refers to an operation until charges generated according to image capturing light (reflected light from a specimen in this example) received by respective pixels are read out when the image capturing unit 11 is a semiconductor image capturing element such as a CMOS sensor or a CCD sensor. CMOS stands for "complementary metal oxide semiconductor image sensor." CCD stands for "charge coupled device."

The light source device 2 includes a plurality of illumination units 15 and a lighting control unit 16 that performs lighting driving of each illumination unit 15. A point light source, a line illumination, or a parallel light illumination may be used as the illumination unit 15. Further, a tungsten lamp, a halogen lamp, a Xenon lamp, a white LED, or the like may be used as a light source type. LED stands for "light emitting diode."

A projector device may be used as the projector 3. The projector 3 irradiates a specimen with a stripe-like projection pattern (a projection pattern having a certain spatial frequency) when the image clarity (definition) and the orange peel of the specimen are measured.

For example, a liquid crystal monitor device may be used as the monitor device 5. As will be described later, for example, a strength histogram corresponding to each irradiation angle of light in a glittering feeling parameter is displayed on the monitor device 5 in addition to a setting menu, an operation menu, and the like.

A common computer device may be used as the information processing device 4. The information processing device 4 includes a CPU 21, a ROM 22, a RAM 23, and a hard disk drive (HDD) 24. The information processing device 4 further includes various kinds of interfaces (I/F) 25 and an input/output interface (I/O) 26. The CPU 21 to the I/O 26 are connected to one another via a bus line 27. CPU stands for "central processing unit." ROM stands for "read only memory." RAM stands for "random access memory."

Figure 2:
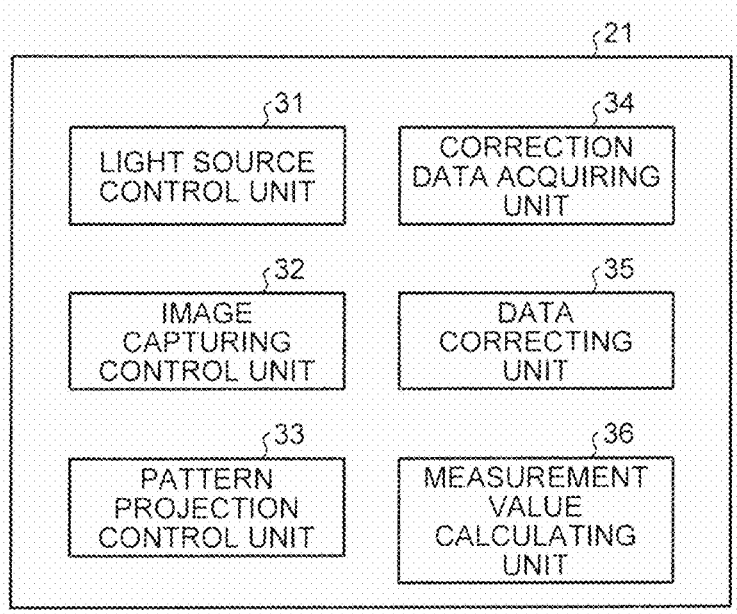
FIG. 2 is a functional block diagram of the specimen measuring device according to the first embodiment.

The HDD 24 stores a specimen measuring program that performs, for example, an operation corresponding to each measurement item of a specimen using acquired spectral information together with image capturing control of the spectral camera device 1, light source lighting control of the light source device 2, and projection control of the projection pattern of the projector in order to measure the texture of a specimen. FIG. 2 is a functional block diagram illustrating functions implemented by the CPU 21 operating according to the specimen measuring program. The CPU 11 implements functions of a light source control unit 31, an image capturing control unit 32, a pattern control unit 33, a correction information acquiring unit 34, an information correcting unit 35, and a measurement value calculating unit 36 serving as a calculating unit in a software manner as illustrated in FIG. 2.

In this example, the light source control unit 31 to the measurement value calculating unit 36 are described as being implemented in the software manner, but some or all of the light source control unit 31 to the measurement value calculating unit 36 may be implemented in a hardware manner.

The specimen measuring program may be recorded in a computer readable recording medium such as a CD-ROM or a flexible disk (FD) in an installable format or an executable format and provided. Further, the specimen measuring program may be recorded in a computer readable recording medium such as a CD-R, a DVD, a Blu-ray disc (a registered trademark), or a semiconductor memory and provided. DVD stands for "digital versatile disk." Furthermore, the specimen measuring program may be provided in a form in which it is installed via a network such as the Internet. Moreover, the specimen measuring program may be installed in an internal ROM or the like in advance and provided.

The light source control unit 31 performs lighting control of the light source device 2. The image capturing control unit 32 performs image capturing control of the spectral camera device 1. The pattern projection control unit 33 projects a certain projection pattern. The correction information acquiring unit 34 acquires correction information by reading, for example, a correction member such as a standard white plate, a standard black glass, or a mirror when a measurement starts. The information correcting unit 35 corrects measurement information of the image clarity, the orange peel, and the like using the acquired correction information. The measurement value calculating unit 36 calculates evaluation values of various kinds of measurement items using the corrected measurement information.

Next, the principle of the spectral camera device 1 will be described with reference to FIG. 3. Here, in order to facilitate understanding, a main lens 54 serving as an optical system is illustrated by a single lens, and a diaphragm position S of the main lens 54 is assumed to be the center of the single lens. A color filter 56 serving as an optical band pass filter is arranged at the center of the main lens 54. The color filter 56 is a filter corresponding to a tristimulus value of a color having spectral transmittance based on a color-matching function of an XYZ color system. In other words, the color filter 56 includes a plurality of color filters (here, three color filters 56a, 56b, and 56c) having different spectral transmittance based on the color-matching function of the XYZ color system.

The optical band pass filter may be configured by combining a plurality of filters having different spectral transmittance or may be configured such that regions of one filter are configured to have different spectral transmittance. For example, when 16 types of optical band pass filters having a peak of a transmission wavelength at intervals of 20 nm in a wavelength region of 400 nm to 700 nm are used, it is possible to acquire spectral information in the wavelength region of 400 nm to 700 nm at intervals of 20 nm.

Figure 3:
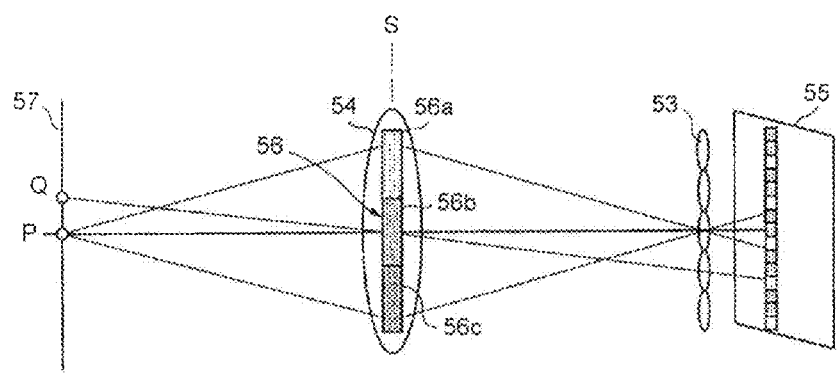
FIG. 3 is a diagram schematically illustrating a main part of a spectral camera device installed in the specimen measuring device according to the first embodiment.

Actually, the color filter 56 is not positioned in the lens as illustrated in FIG. 3. The color filter 56 is arranged nearby the diaphragm of the main lens 54. "Nearby the diaphragm" means a portion that includes a diaphragm position and is allowed to transmit light beams of various angles of view. In other words, it means a design permissible range of the color filter 56 on the main lens 54.

Figure 4:
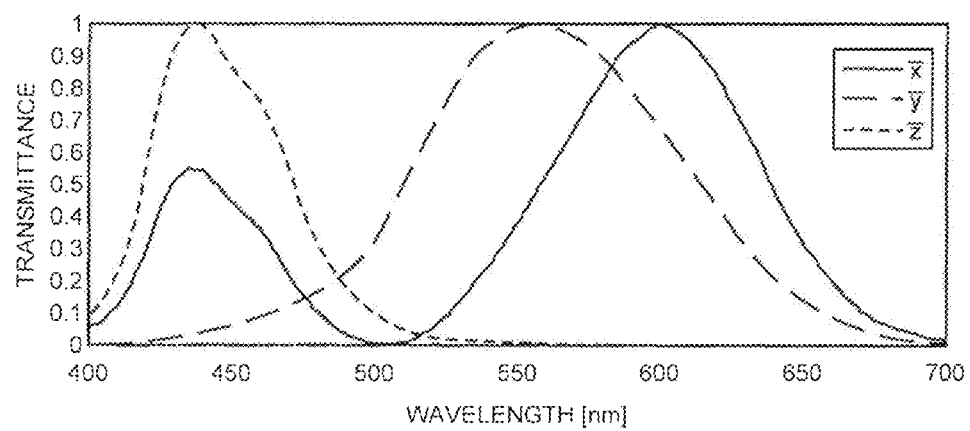
FIG. 4 is a diagram illustrating spectral transmittance of respective color filters when an incidence angle of light beams is 0° in the spectral camera device of the specimen measuring device according to the first embodiment.

FIG. 4 illustrates spectral transmittance of the color filters 56a, 56b, and 56c when an incidence angle of light beams is 0°. In FIG. 4, a solid line, a broken line, and a dotted line indicate spectral transmittance $T_X(\lambda)$, $T_Y(\lambda)$, and $T_Z(\lambda)$ of the color filters 56a ($F_X$), 56b ($F_Y$), and 56c ($F_Z$) based on the following color-matching function, respectively.

Figure 5:
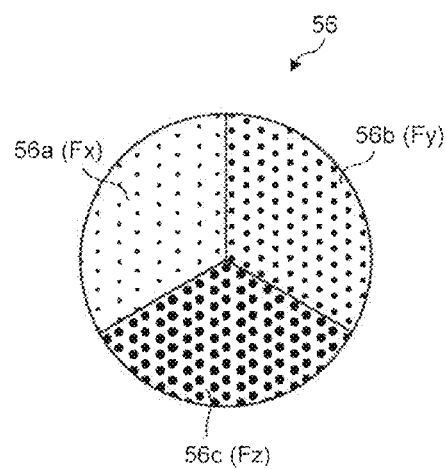
FIG. 5 is a diagram illustrating a geometric design example of a color filter of the spectral camera device of the specimen measuring device according to the first embodiment.

FIG. 5 illustrates a geometric design example of the color filters 56a ($F_X$), 56b ($F_Y$), and 56c ($F_Z$). In FIG. 5, the color filter 56 is divided into three equal fan shapes, but the entire shape of the color filter 56 may be a circular shape or a rectangular shape. Further, the respective filters need not necessarily have the same area ratio.

As illustrated in FIG. 4, an area surrounded by a line of a color-matching function for Z is smaller than other areas. The area size correlates with a magnitude of a signal to noise (SN) ratio. In order to increase the SN ratio, the area of the color filter 56c corresponding to Z may be increased to be larger than the other areas.

Figure 6:
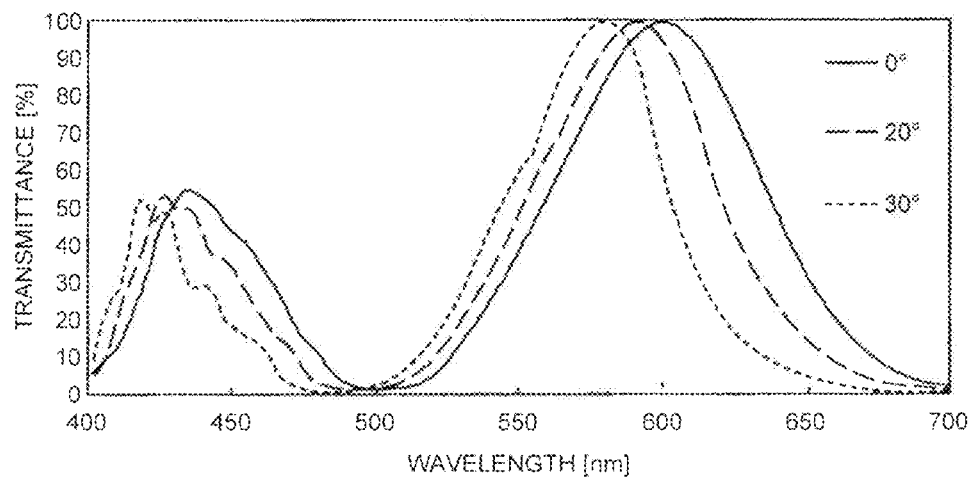
FIG. 6 is a characteristic diagram illustrating dependence of spectral transmittance of a color filter on an incidence angle.

Next, a design of $T_X(\lambda)$, $T_Y(\lambda)$, $T_Z(\lambda)$ will be described. Each spectral transmittance of FIG. 6 is designated based on a color-matching function specified in the CIE-1931 color system, spectral transmittance $T_L(\lambda)$ of an optical system excluding a filter of a lens, and spectral sensitivity $S(\lambda)$ of a light receiving element. In other words, each spectral transmittance of FIG. 6 is defined as in the following Formulas (1) to (3):

$$T'_X(\lambda) = \bar{x}(\lambda)/\{S(\lambda)T_L(\lambda)\} \quad (1)$$

$$T'_Y(\lambda) = \bar{y}(\lambda)/\{S(\lambda)T_L(\lambda)\} \quad (2)$$

$$T'_Z(\lambda) = \bar{z}(\lambda)/\{S(\lambda)T_L(\lambda)\} \quad (3)$$

In Formulas (1) to (3), since a sensor has its own spectral sensitivity, it is divided by $S(\lambda)$ in order to remove non-uniformity. In Formulas (1) to (3), transmittance standardized under the assumption that each maximum value is transmittance of 100% is $T_X(\lambda)$, $T_Y(\lambda)$, and $T_Z(\lambda)$. Particularly, the SN ratios of the color filters corresponding to $x(\lambda)$ and $y(\lambda)$ can be improved through the standardization. Using the color filter designed as described above, when the light beams transmitting the color filter are detected by the light receiving element, it is possible not only to back-calculate standardization by a maximum value but also to use output values as X, Y, and Z (tristimulus values) without change.

$T_X(\lambda)$, $T_Y(\lambda)$, and $T_Z(\lambda)$ are complicated waveforms but can be generated by a value close to a design value. For example, $T_X(\lambda)$, $T_Y(\lambda)$, and $T_Z(\lambda)$ can be generated by a dielectric multi-layer film. The dielectric multi-layer film functions as a band pass filter due to an optical interference action. Since a band pass filter can be implemented by an interference action, the spectral transmittance of the color filter 56 has a dependence on the incidence angle of light beams in principle. FIG. 6 illustrates a dependence on an incidence angle in the color filter 56a ($F_X$). A solid line, a broken line, and a dotted line indicate spectral transmittance when an incidence angle is 0°, 20°, and 30°. It is understood that as the incidence angle is increased, the transmission region is shifted toward a short wavelength side.

A micro lens array (MLA) 53 configured with a plurality of micro lenses (small lenses) is arranged nearby a condensing position of the main lens 54 as illustrated in FIG. 3. A light receiving element array 55 including a plurality of light receiving elements (sensors) each of which converts optical information condensed by the main lens 54 into electronic information (electrical signal) is arranged on an image plane. The diameter of the micro lens of the MLA 53 and each of the light receiving elements configuring the light receiving element array 55 are in a relation of a ratio of about "30:1 to 2:1."

Figure 7:
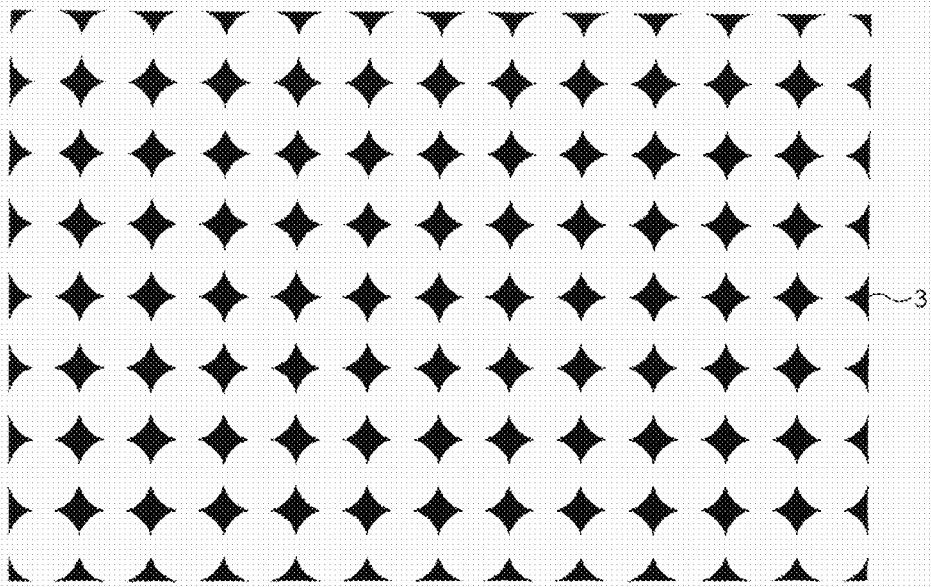
FIG. 7 is a diagram illustrating an lens array viewed in an optical axis direction.

FIG. 7 is a diagram of an MLA 3 viewed in an optical axis direction. In FIG. 7, white circles indicate lenses, and black portions indicate light-shielding portions. In other words, portions other than portions of lenses configuring the lens array are light-shielded by the light-shielding portion. For example, the light-shielding portion is formed by performing vapor deposition on chromium oxides. The light-shielding portion is a flat portion having no curvature and a region curvature of which does not satisfy a design value specification when manufactured. Since light beams that are not intended by a design in light from the regions may reach the light receiving element, an electrical signal assumed by a design can be obtained by shielding the light. As a result, it is possible to obtain an accurate measurement value.

The light receiving element array 55 is a monochrome sensor in which a color filter of each pixel is not mounted. Hereinafter, a light receiving element array is also referred to as a "monochrome sensor." Among light emitted from an object 57 illustrated in FIG. 3, light flux that is incident on an opening of the main lens 54 and passes through the diaphragm is a measurement target. The light flux incident on the main lens is a set of innumerable light beams, and the respective light beams pass through different positions of the diaphragm of the main lens 54. In the case of the example of FIG. 3, since the three color filters 56a, 56b, and 56c are arranged at the diaphragm position of the main lens 54, the light beams pass through the three filters having different spectral transmittance. At this time, an angle of the light beams incident on the filter plane differs according to the height of an object. It is understood from the fact that main light beams of the light flux emitted from points on the object indicated by signs P and Q in FIG. 3 pass through the diaphragm plane of the main lens 54 at different angles.

The light beams that have passed through the color filter 56 first form an image nearby the MLA 53 but then arrive at different positions of the respective sensors by the MLA 53. In other words, since the position (the light receiving position) of the sensor surface corresponds to the filter plane through which the light beams have passed, it is possible to measure values obtained by separating light emitted from a certain point of the object into the tristimulus values X, Y, and Z in terms of a wavelength.

However, since the spectral transmittance of the color filter 56 has the dependence on the incidence angle as described above with reference to FIG. 6, when an output of the light receiving element is simply used, it is difficult to measure the accurate tristimulus values X, Y, and Z of an off-axis 2D plane other than an optical axis.

For this reason, the spectral camera device 1 is configured to obtain the accurate tristimulus values of the 2D plane which are corrected for each light receiving position using a reference value and a value calculated from an output value from the spectral camera device 1. Generally, there is a technique called multiple regression analysis. In the multiple regression analysis, an explanatory variable and an objective variable are prepared in advance, and a correction operation is performed using a regressor matrix obtained from the explanatory variable and the objective variable. A procedure thereof will be specifically described below. First, a procedure of calculating an output value from the spectral camera device 1 will be described. This corresponds to the explanatory variable in the multiple regression analysis.

Figure 8:
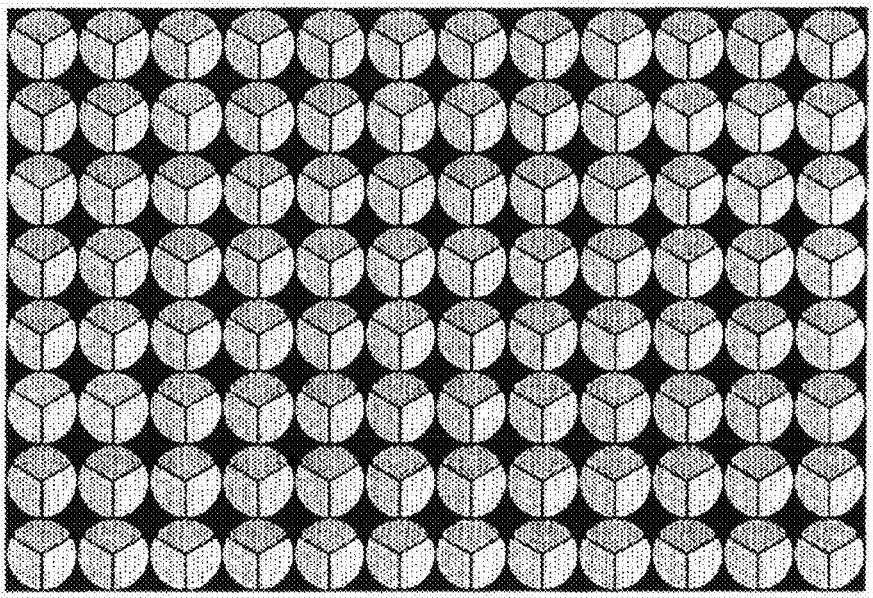
FIG. 8 is a plane view of a captured image of a spectral camera device.
Figure 9:
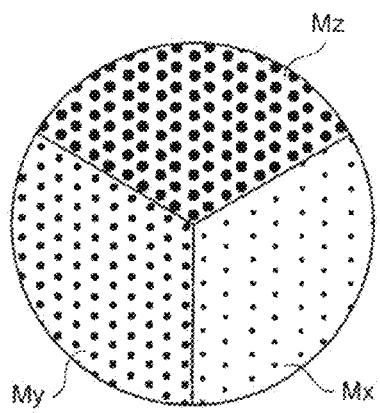
FIG. 9 is an enlarged view of a macro pixel configuring the image of FIG. 8.

An image captured through the configuration of FIG. 3 is one in which small circles are arranged as illustrated in FIG. 8. The circles are formed because a diaphragm of a single lens (the main lens 54) has a circular shape. Here, the small circles are referred to as "macro pixels." Each macro pixel is formed directly below each of small lenses configuring a lens array. A macro pixel has an internal structure corresponding to the structure of the color filter illustrated in FIG. 5. FIG. 9 is an enlarged view of a macro pixel. When FIG. 9 is compared with FIG. 5, the diagram is reversed horizontally and vertically because it has passed through the optical system. Here, since a correspondence relation depends on the optical system, the present invention is not limited to this example.

Each of the internal structures $M_X$, $M_Y$, and $M_Z$ of the macro pixel is a result obtained as light having passed through the color filters $F_X$, $F_Y$, and $F_Z$ has arrived. An output value of the light receiving elements of $M_X$, $M_Y$, and $M_Z$ is assumed to be $v=[v_X, v_Y, v_Z]^t$. t means a transpose of matrix. As the output value, an average value of $M_X$, $M_Y$, and $M_Z$ may be used, and one light receiving element is selected from $M_X$, $M_Y$, and $M_Z$, and an output value of the selected light receiving element may be used as a representative value.

Figure 10:
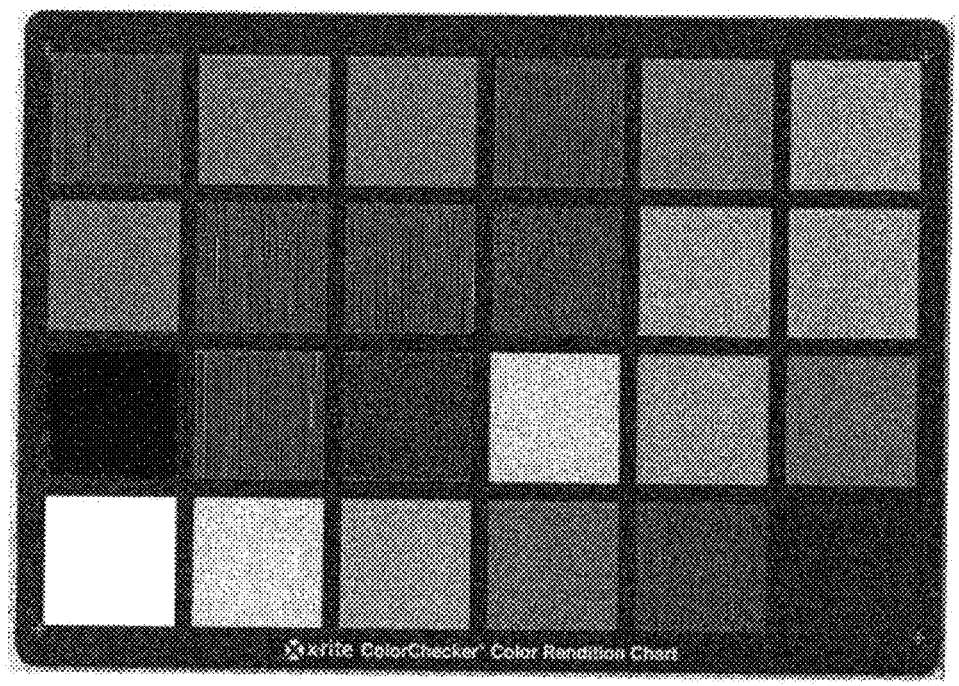
FIG. 10 is a diagram illustrating an example of a color checker serving as a color sample.
Figure 11:
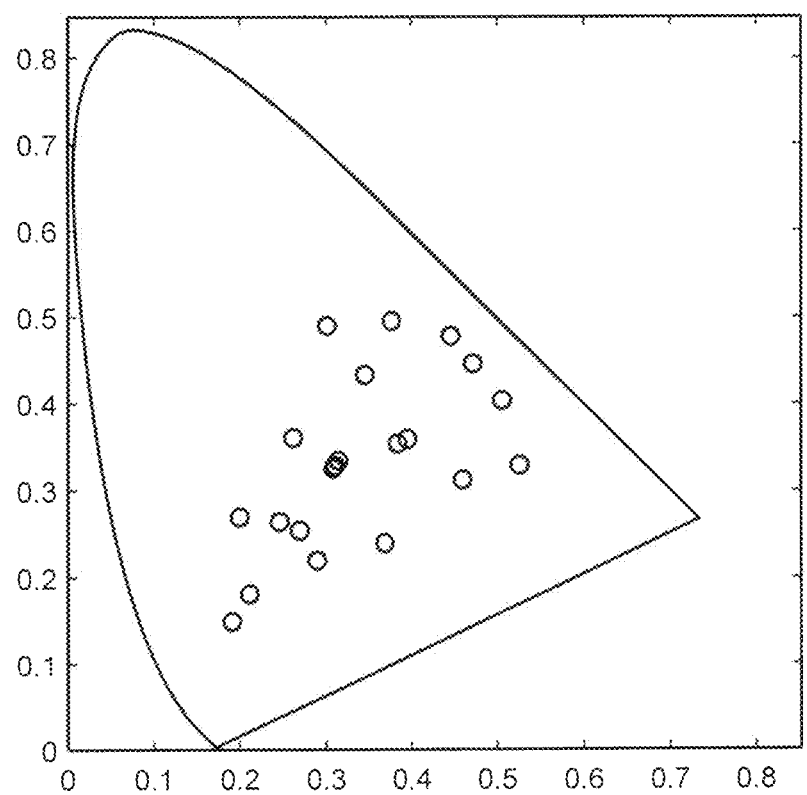
FIG. 11 is a plot diagram in which 24 colors of a color checker are plotted as an xy chromaticity diagram.

Next, a method of acquiring the reference value will be described. This corresponds to the objective variable in the multiple regression analysis. A color sample covering a wide range in a color space is measured through a device that measures an X value, a Y value, and a Z value of a spectroscope or the like, and the measured value is used as the reference value. As the color sample, for example, a "color checker", which is widely used, in which rectangular color samples of 24 colors are arranged may be used. FIG. 10 illustrates an example of the color checker. FIG. 11 illustrates a result of plotting measurement values of the 24 colors included in the color checker as an xy chromaticity diagram.

The color sample is not limited to the color checker, and when a target that is desired to be measured is known, a better correction result can be obtained by using a value close to the color as the reference value. The reference value of X, Y, and Z (the tristimulus values) on a certain color sample is assumed to be $r=[r_X, r_Y, r_Z]^t$.

Next, the flow of the correction operation will be described. First, the reference value is obtained by measuring a color sample through a measuring device. When a 24-color color checker is used as the color sample, numbering is performed for the sake of convenience, and a reference value on a first color is assumed to be $r_1=[r_{1X}\ r_{1Y}\ r_{1Z}]^t$. In other words, values of $r_1$ to $r_{24}$ are obtained. R is assumed to be $[r_1, r_{24}]$. R is a 3×24 matrix. The matrix R is the objective variable.

Then, an image of the color sample is captured through the spectral camera device 1 of FIG. 3 to acquire image capturing information. At this time, an arrangement is performed so that one color sample is shown in the entire image. v is acquired from each macro pixel. $V=[v1, \ldots, v_{24}]$ is obtained, similarly to the reference value. V is the explanatory variable. A matrix G is obtained from R and V obtained herein.

$$G=RV^t(VV^t)^{-1} \qquad (4)$$

The matrix G is called a regressor matrix and used for a correction operation. Since the explanatory variable V has a different value according to each macro pixel, the matrix G is calculated for each macro pixel as well. This is preparation for the correction operation.

The flow when an actual measurement is performed will be described. An image of a specimen serving as a measurement target is captured through the spectral camera device 1. An output value for each macro pixel included in the captured image is calculated. The output value is assumed to be "$v_C=[v_{CX}, v_{CY}, v_{CZ}]^t$" Then, a corrected tristimulus value $r_c$ is calculated by performing an operation of the following Formula (5). By obtaining $r_c$ for each macro pixel, it is possible to obtain an accurate tristimulus value of a 2D plane.

$$r_C = G v_C \quad (5)$$

The above-described flow, V or $v_c$ is used without change as the output value, but it is possible to expand as expressed in the following Formula (6).

$$v = [v_X, v_Y, v_Z, 1 v_X^2 v_Y^2 v_Z^2 \ldots]^t \quad (6)$$

" . . . " of Formula (6) means a high-order term such as $v_X v_Y$ and $v_X^3$. By performing such extension, it is possible to increase the correction accuracy and thus obtain a more accurate value. When the regressor matrix G is obtained based on extended V, it is desirable to use extended $v_C$ even in the case of the measurement using Formula (5) actually.

Figure 12:
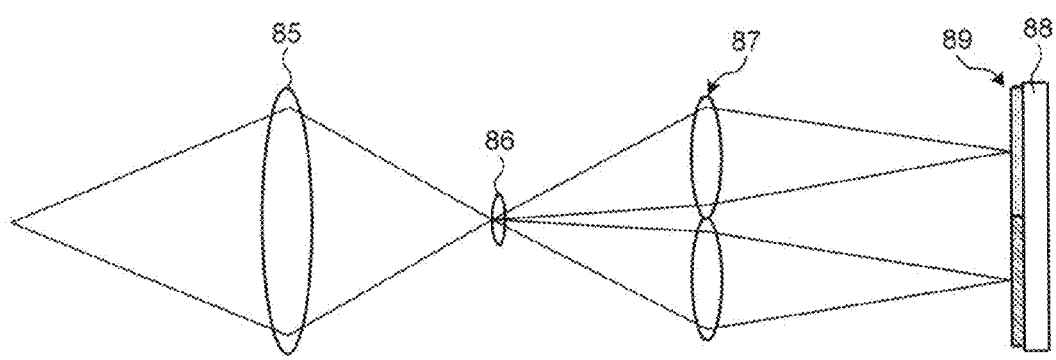
FIG. 12 is a diagram schematically illustrating a main part of another spectral camera device installed in the specimen measuring device according to the first embodiment.
Figure 13:
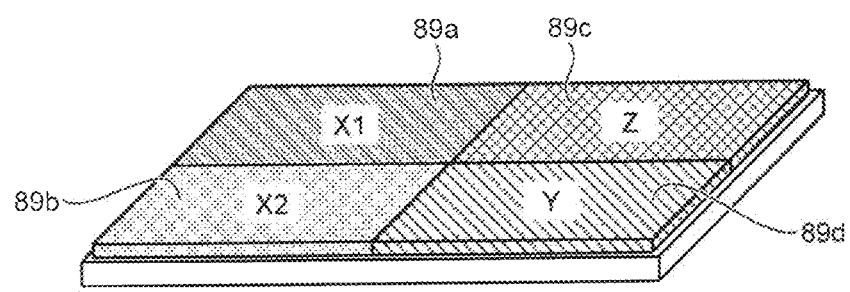
FIG. 13 is a diagram for describing a spectral filter installed on a sensor surface of another spectral camera device.

Next, the spectral camera device having the configuration of FIG. 12 may be used as the spectral camera device 1. In the case of the spectral camera device 1 illustrated in FIG. 12, a micro lens array 87 is installed so that an image position of a main lens 85 and a sensor surface 88 have a conjugate relation. Further, by installing a plurality of spectral filters 89a to 89d on a sensor surface 88 as illustrated in FIG. 13, the same effects as described above can be obtained.

In the case of the spectral camera device 1 illustrated in FIG. 12, the number of lenses of the micro lens array 87 is the same as the number of spectral filters 89a to 89d. Further, an image of the main lens 85 is formed at each sensor position through each micro lens array 87. In the case of the spectral camera device 1 illustrated in FIG. 12, since complicated image processing is unnecessary, a high-speed operation can be performed. Further, since respective spectral images can be simultaneously captured in image capturing regions adjacent to each other, it is possible to effectively use the sensor surface 88, and it is possible to obtain a spectral image having a higher resolution than in the spectral camera device 1 described with reference to FIG. 3 or the like.

Further, a field lens 86 may be installed between the main lens 85 and the micro lens array 87. As the field lens 86 is installed, it is possible to reduce parallax of an image generated by each micro lens array 87. Further, the field lens 86 is preferably configured such that an exit pupil of the main lens 85 has a conjugate relation with an entrance pupil of the micro lens array 87.

Next, FIG. 14 illustrates a positional relation of the spectral camera device 1 and the illumination units 15 of the light source device 2 in the specimen measuring device according to the embodiment. FIG. 15 illustrates angles formed by the positional relation of the spectral camera device 1 and the illumination units 15 of the light source device 2.

The specimen measuring device according to the embodiment emits light from each of illumination units 15a to 15e of the light source device 2 that are arranged at two or more angles with respect to a plane specimen 61. Further, the spectral camera device 1 arranged, for example, in a vertical direction (directly above the specimen 61) with respect to the specimen 61 or above the specimen 61 (obliquely above the specimen 61) as illustrated in FIG. 14 acquires 2D spectral information of the specimen 61 through a single image capturing operation (one shot) for each irradiation angle of light of the illumination units 15a to 15e. In this case, the specimen measuring device sets difference angles (aspecular angles) between an irradiation angle and a mirror surface reflection angle of light in a right end 61a and a left end 61b of the specimen 61 and a viewing angle of the spectral camera device 1 in the right end 61a and the left end 61b of the specimen 61 according to a size of the specimen 61, a subject distance, and an angle of view of the spectral camera device 1 under the following condition. Further, the deflection angle spectral information of the specimen surface of the specimen 61 is acquired in a deflection angle range determined according to the position of the spectral camera device 1 without omission.

For example, when deflection angle spectral information of a range of −15° to 110° is acquired, the spectral camera device 1 is installed at an angle of 45° with respect to the specimen 61 as illustrated in FIGS. 14 and 15. Further, the illuminations are arranged so that "angle A≤−15°≤angle C≤angle B≤angle E≤angle D≤angle G≤angle F≤angle I≤angle H≤110°≤angle J" is satisfied as an aspecular angle as illustrated in FIGS. 14 and 15, and spectral information (deflection angle spectral information) of a desired deflection angle range is acquired without omission.

Figure 16:
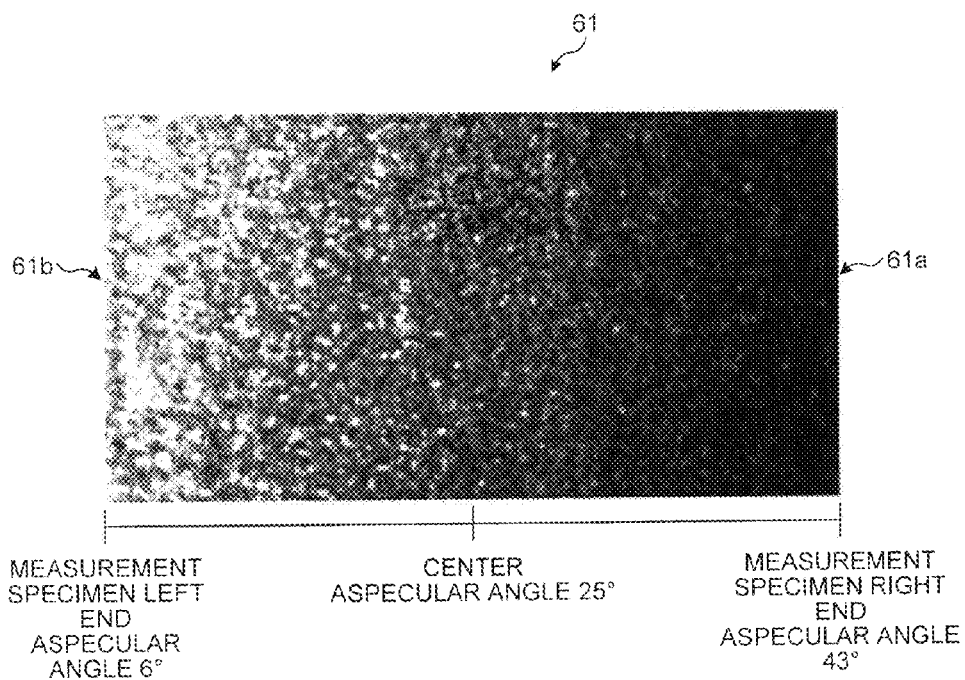
FIG. 16 is a diagram illustrating an example of a captured image captured by a spectral camera device at a timing at which light is emitted from an illumination unit.

FIG. 16 illustrates an example of a captured image captured by the spectral camera device 1 at a timing at which light is emitted from the illumination unit 15d. In the image capturing performed using the illumination unit 15d, light from the illumination unit 15d is emitted to the specimen 61 from a location slightly close to the right end 61a of the specimen 61. Further, the spectral camera device 1 receives reflected light of the light emitted to the specimen 61 from a location slightly close to the left end 61b of the specimen 61 and captures an image of the specimen 61. For this reason, the illumination direction of the light is opposite to the image capturing direction, and thus the captured image of the specimen 61 that is getting darker gradually from the left end 61b of the specimen 61 to the right end 61a of the specimen 61 as illustrated in FIG. 16 is captured.

In the configuration of FIG. 14, as an example, the diameter of the specimen 61 is assumed to be 60 mm, a distance between the spectral camera device 1 having the angle of view of 22.6° and the specimen 61 is assumed to be 150 mm, and a distance between the specimen 61 and each of the illumination units 15a to 15e arranged at the respective angles is assumed to be 150 mm. In this case, a maximum deflection angle range that can be acquired is set to −16° to 121° as illustrated in FIG. 15. When the number of illumination units is increased under the same condition, the deflection angle range is set to a maximum of −54° to 142°.

Figure 17:
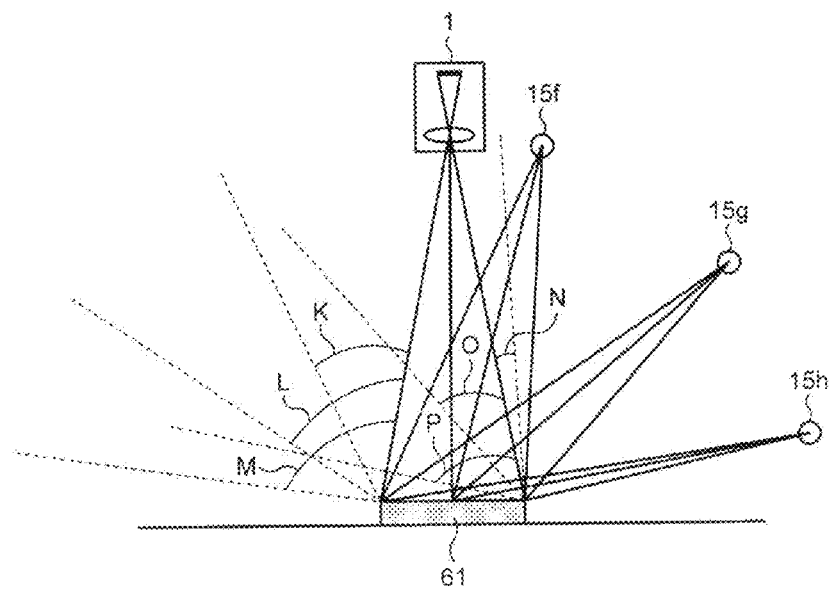
FIG. 17 is a diagram illustrating another positional relation of a spectral camera device and illumination units of a light source device in the specimen measuring device according to the first embodiment.

On the other hand, when deflection angle spectral information of a range of 0° to 90° is acquired, the spectral camera device 1 is installed vertically to the specimen 61 as illustrated in FIG. 17. Further, illumination units 15f to 15h are installed so that a condition of "angle N≤0°≤angle O≤angle K≤angle P≤angle L≤90°≤angle M" is satisfied as an aspecular angle, and it is possible to acquire the deflection angle spectral information of the coverage range without omission. In the example of FIG. 17, the three illumination units 15f to 15h are installed as the illumination unit, but the number of illumination units may be determined according to the size of the specimen 61, the subject distance, the angle of view of the spectral camera device 1, or the deflection angle range that is desired to be measured.

In the configuration illustrated in FIG. 17, the diameter of the specimen 61 is assumed to be 60 mm, the distance between the spectral camera device 1 and the specimen 61 is assumed to be 150 mm, and the distance between the specimen 61 and each of the illumination units 15f to 15h installed at the respective angles is assumed to be 150 mm. In this case, a maximum deflection angle range that can be acquired is −23° to 101°. In the ASTM criterion (E2539), −15° to 110° is employed as a normal aspecular angle for a pearlescent color. ASTM stands for American Society for Testing and Materials. However, depending on a specimen, there are cases in which it is possible to perform measurement capable of detecting features of a specimen even at an aspecular angle of 0° to 90°. Thus, it is desirable to use the configuration of FIG. 14 and the configuration of FIG. 17 differently according to a specimen.

Next, an operation of measuring the specimen 61 and an operation of calculating a measurement value of each evaluation item will be described. First, an overview of an operation will be described. In FIG. 1, the information processing device 4 performs the image capturing control of the spectral camera device 1 through the image capturing control unit 32 illustrated in FIG. 2. Further, the information processing device 4 performs the lighting control of the illumination unit 15 through the light source control unit 31, and calculates a measurement value of each evaluation item through the measurement value calculating unit 36. Each calculated measurement value is stored in a storage unit such as the HDD 24, the RAM 23, or the ROM 22.

Further, before measuring the specimen, the information processing device 4 reads the correction member such as the standard white plate through the correction information acquiring unit 34, and generates the correction information used to correct the deflection angle spectral information. Furthermore, when measuring the image clarity and the orange peel, the information processing device 4 reads the correction member such as a uniform standard black glass or a uniform standard mirror through the correction information acquiring unit 34, and generates the correction information used to correct the deflection angle spectral information. The correction information acquiring unit 34 stores the generated correction information in the storage unit such as the HDD 24, the RAM 23, or the ROM 22. The information correcting unit 35 corrects the deflection angle spectral information of the specimen obtained by the measuring using the correction information. The measurement value calculating unit 36 calculates a measurement value of each evaluation item using the corrected deflection angle spectral information. The correction information may be generated before the specimen is measured, for example, at the time of shipping from a factory or may be generated each time the specimen is measured by always having the correction member ready.

Figure 18:
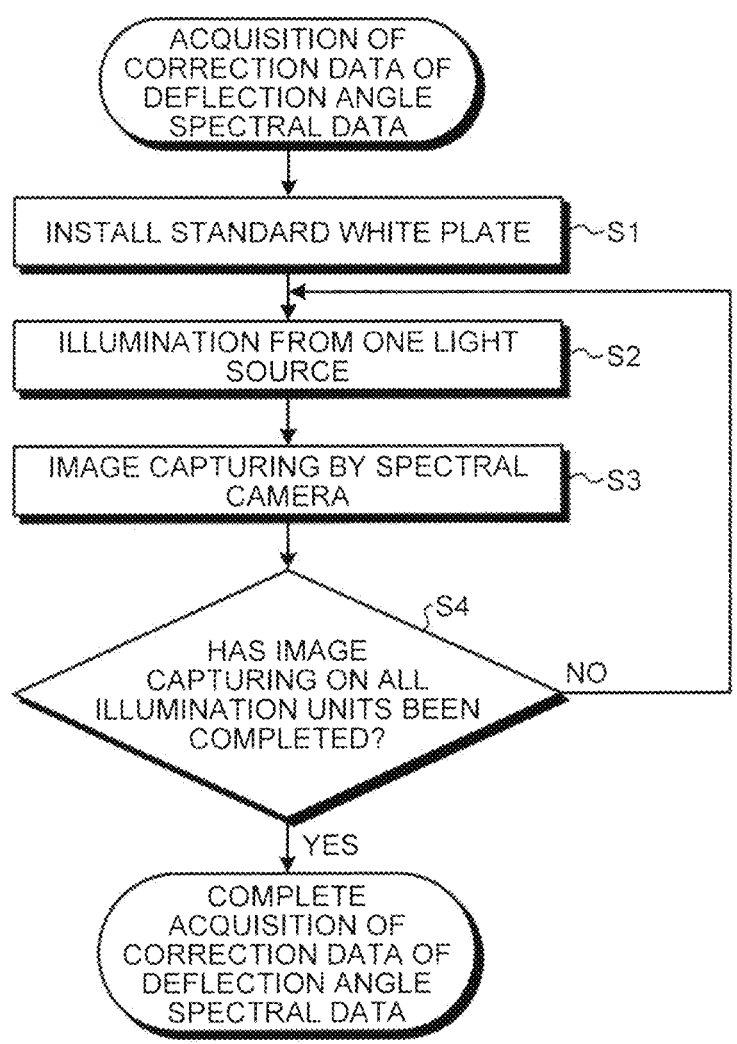
FIG. 18 is a flowchart for describing an acquisition operation of correction information of deflection angle spectral information in the specimen measuring device according to the first embodiment.

A concrete description will be given below. First, FIG. 18 is a flowchart illustrating the flow of an acquisition operation of normal correction information other than the correction information corresponding to the image clarity and the orange peel. In the flowchart of FIG. 18, in step S1, a transfer mechanism of the standard white plate is controlled manually by the user or the correction information acquiring unit 34 such that the standard white plate is installed at an installation position (within an image capturing range of the spectral camera device 1) of the specimen 61 illustrated in FIG. 14 or FIG. 17.

In step S2, the light source control unit 31 performs the lighting control on any one of the illumination units 15a to 15e illustrated in FIG. 14 or any one of the illumination units 15f to 15h illustrated in FIG. 17. In step S3, the image capturing control unit 32 performs the image capturing control on the spectral camera device 1 such that an image of the standard white plate irradiated with the light from the illumination unit that has undergone the lighting control is captured through one shot. The correction information acquiring unit 34 stores the image capturing information of the standard white plate in the storage unit such as the HDD 24 of FIG. 1 as the correction information.

The specimen measuring device according to the embodiment captures an image of the standard white plate while performing the lighting control on the illumination units sequentially one by one. In step S4, the CPU 21 determines whether or not image capturing corresponding to all the illumination units has been completed. When the CPU 21 determines that the image capturing corresponding to all the illumination units has not been completed (No in step S4), the process returns to step S2. Then, the light source control unit 31 performs the lighting driving on the illumination unit that undergoes the lighting driving next again, and the image capturing of the standard white plate by the spectral camera device 1 is repeated under control of the image capturing control unit 32. As a result, each correction information corresponding to each illumination unit is stored in the HDD 24.

On the other hand, when the image capturing corresponding to all the illumination units is determined to have been completed (Yes in step S4), the process of the flowchart of FIG. 18 ends.

Figure 19:
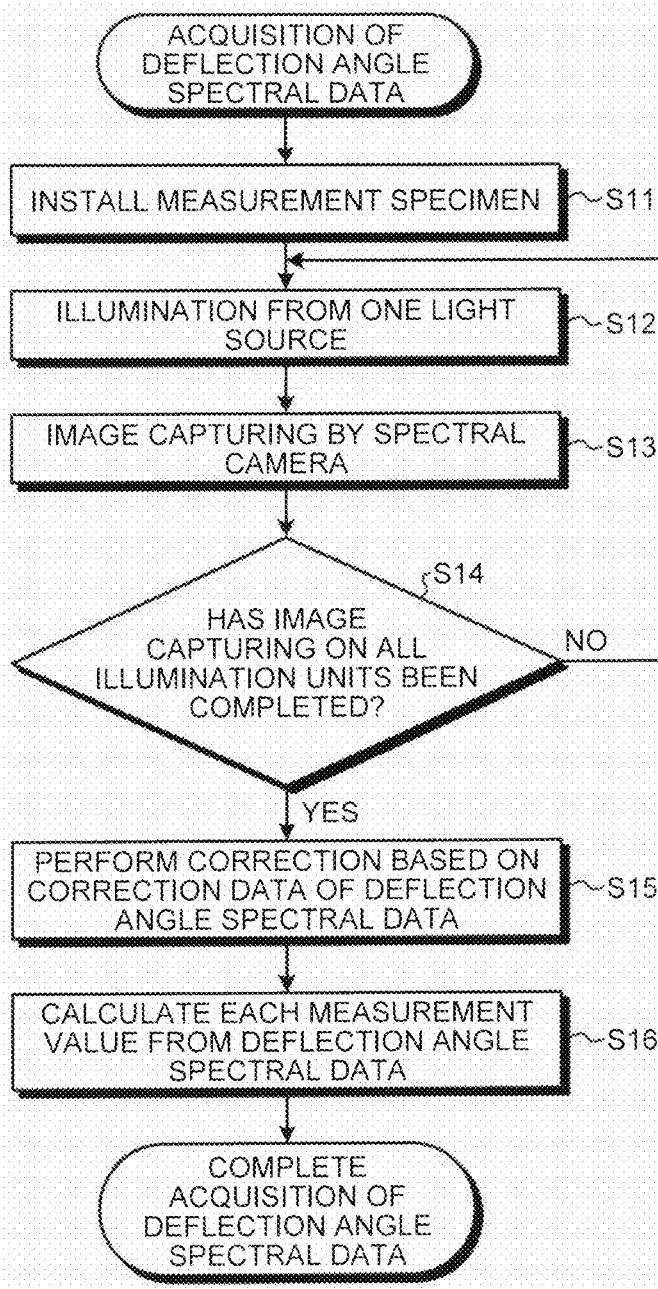
FIG. 19 is a flowchart for describing an acquisition operation of deflection angle spectral information in the specimen measuring device according to the first embodiment.

As illustrated in a flowchart of FIG. 19, when the correction information is acquired as described above, the specimen measuring device according to the embodiment acquires polarization spectral information of each illumination unit by capturing an image of the specimen, and calculates a measurement value of each evaluation item using each polarization spectral information. Referring to the flowchart of FIG. 19, in step S11, the transfer mechanism is controlled manually by the user or the correction information acquiring unit 34 such that the specimen 61 is installed within the image capturing range of the spectral camera device 1 as illustrated in FIG. 14 or FIG. 17.

In step S12, the light source control unit 31 performs the lighting control on any one of the illumination units 15a to 15e illustrated in FIG. 14 or any one of the illumination units 15f to 15h illustrated in FIG. 17. In step S13, the image capturing control unit 32 performs the image capturing control on the spectral camera device 1 such that an image of the specimen 61 irradiated with the light from the illumination unit that has undergone the lighting control is captured through one shot. The image capturing control unit 32 stores the deflection angle spectral information serving as the image capturing information of the specimen 61 in the storage unit such as the RAM 23 of FIG. 1.

Here, the specimen measuring device performs either or both of an operation (an operation of changing a quantity of light) in which the light source control unit 31 performs the lighting control of the illumination units 15a to 15e and an operation in which the image capturing control unit 32 changes an exposure time at the time of image capturing so that a certain exposure time is obtained. Then, the measurement value calculating unit 36 synthesizes a plurality of pieces of 2D spectral information acquired according to a change in a quantity of light or a change in an exposure time. As a result, it is possible to generate 2D spectral information having an enlarged dynamic range.

Then, the specimen measuring device according to the embodiment captures an image of the specimen 61 while performing the lighting control on the illumination units sequentially one by one. In step S14, the CPU 21 determines whether or not image capturing corresponding to all the illumination units has been completed. When the CPU 21 determines that the image capturing corresponding to all the illumination units has not been completed (No in step S14), the process returns to step S12. Then, the light source control unit 31 performs the lighting driving on the illumination unit that undergoes the lighting driving next again, and the image capturing of the specimen 61 by the spectral camera device 1 is repeated under control of the image capturing control unit 32. As a result, each deflection angle spectral information corresponding to each illumination unit is stored in the HDD 24.

Then, when the image capturing corresponding to all the illumination units is determined to have been completed in step S14 (Yes in step S14), the process proceeds to step S15, and then the information correcting unit 35 corrects each deflection angle spectral information stored in the RAM 23 using the correction information stored in the HDD 24. In step S16, the measurement value calculating unit 36 calculates the measurement value of each evaluation item using the corrected deflection angle spectral information as will be described later. Specifically, the measurement value calculating unit 36 calculates the measurement values of the deflection angle spectral information, the deflection angle color measurement information, the BRDF information, the glittering feeling, the graininess, the gloss, and the haze, and stores the calculated measurement values in the storage unit such as the HDD 24, and then the process of the flowchart of FIG. 19 ends.

Figure 20:
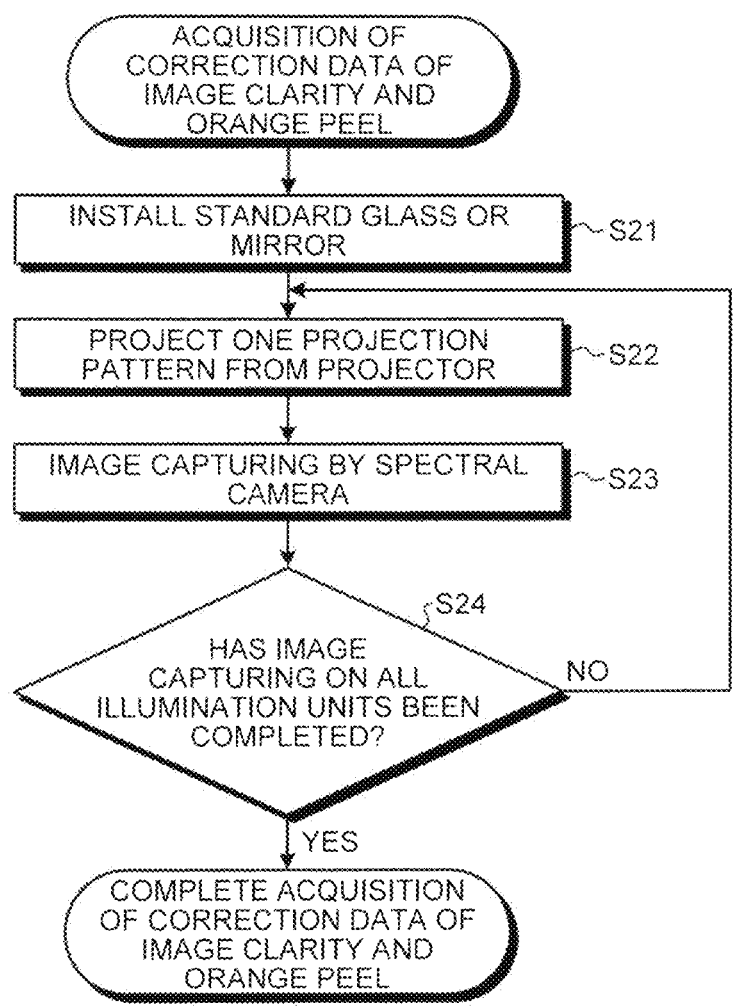
FIG. 20 is a flowchart for describing an acquisition operation of correction information of measurement information of image clarity and orange peel in the specimen measuring device according to the first embodiment.

Next, FIG. 20 is a flowchart illustrating the flow of an acquisition operation of the correction information corresponding to the image clarity and the orange peel. Referring to the flowchart of FIG. 20, in step S21, a transfer mechanism of the standard black glass or the mirror is controlled manually by the user or the correction information acquiring unit 34 such that the standard black glass or the like is installed at an installation position (within an image capturing range of the spectral camera device 1) of the specimen 61 illustrated in FIG. 14 or FIG. 17.

In step S22, the light source control unit 31 performs the lighting control on any one of the illumination units 15a to 15e illustrated in FIG. 14 or any one of the illumination units 15f to 15h illustrated in FIG. 17. Further, in step S23, the image capturing control unit 32 performs the image capturing control on the spectral camera device 1 such that an image of the standard black glass or the like irradiated with the light from the illumination unit that has undergone the lighting control is captured through one shot. The correction information acquiring unit 34 stores the image capturing information of the standard black glass or the like in the storage unit such as the HDD 24 of FIG. 1 as the correction information corresponding to the image clarity and the orange peel.

The specimen measuring device according to the embodiment captures an image of the standard black glass or the like while performing the lighting control on the illumination units sequentially one by one. In step S24, the CPU 21 determines whether or not image capturing corresponding to all the illumination units has been completed. When the CPU 21 determines that the image capturing corresponding to all the illumination units has not been completed (No in step S24), the process returns to step S22. Then, the light source control unit 31 performs the lighting driving on the illumination unit that undergoes the lighting driving next again, and the image capturing of the standard black glass or the like by the spectral camera device 1 is repeated under control of the image capturing control unit 32. As a result, each correction information of the image clarity and the orange peel corresponding to each illumination unit is stored in the HDD 24.

On the other hand, when the image capturing corresponding to all the illumination units is determined to have been completed (Yes in step S24), the process of the flowchart of FIG. 20 ends.

Figure 21:
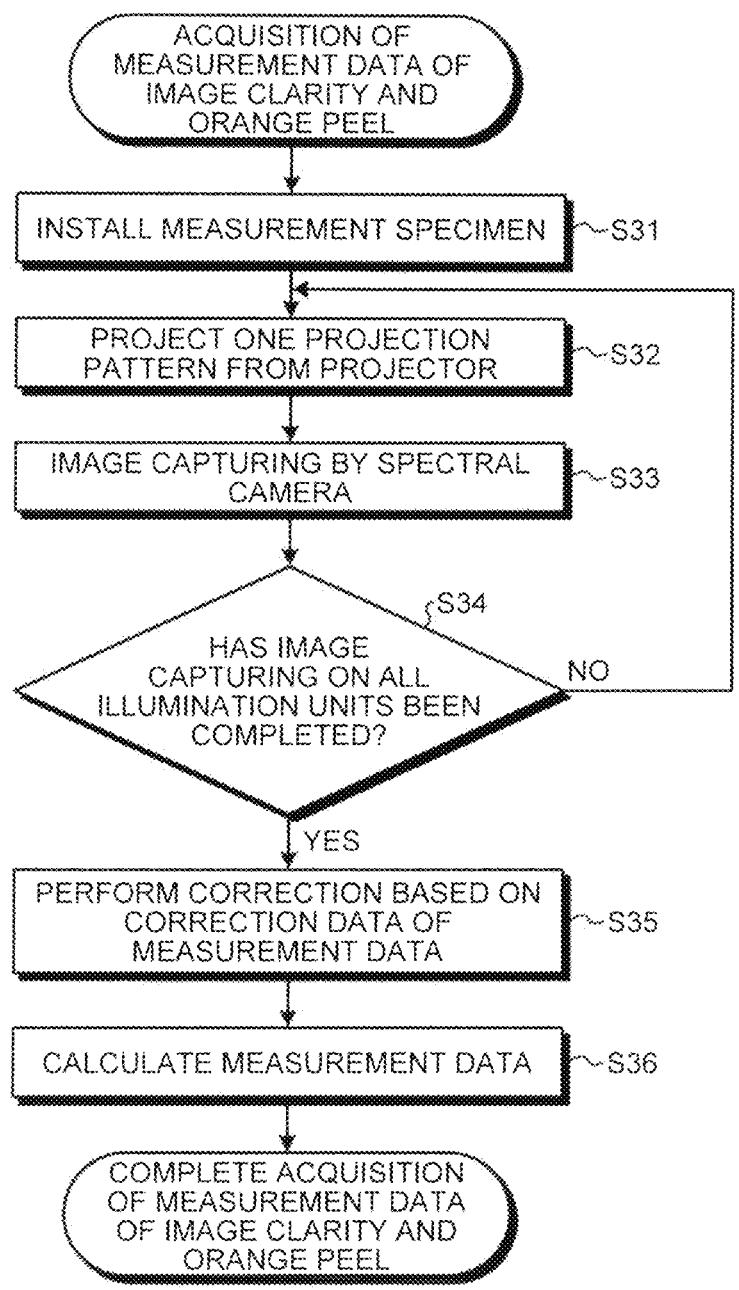
FIG. 21 is a flowchart for describing an acquisition operation of measurement information of image clarity and orange peel in the specimen measuring device according to the first embodiment.

Then, when each correction information of the image clarity and the orange peel is acquired as described above, the specimen measuring device according to the embodiment acquires polarization spectral information of each illumination unit by capturing an image of the specimen, and calculates a measurement value of each evaluation item of the image clarity and the orange peel using each polarization spectral information, as illustrated in a flowchart of FIG. 21.

Referring to the flowchart of FIG. 21, in step S31, the transfer mechanism is controlled manually by the user or the correction information acquiring unit 34 such that the specimen 61 is installed within the image capturing range of the spectral camera device 1 as illustrated in FIG. 14 or FIG. 17. In step S32, the light source control unit 31 performs the lighting control on any one of the illumination units 15a to 15e illustrated in FIG. 14 or any one of the illumination units 15f to 15h illustrated in FIG. 17. In step S33, the image capturing control unit 32 performs the image capturing control on the spectral camera device 1 such that an image of the specimen 61 irradiated with the light from the illumination unit that has undergone the lighting control is captured through one shot. The image capturing control unit 32 stores the deflection angle spectral information serving as the image capturing information of the specimen 61 in the storage unit such as the RAM 23 of FIG. 1.

Then, the specimen measuring device according to the embodiment captures an image of the specimen 61 while performing the lighting control on the illumination units sequentially one by one. In step S34, the CPU 21 determines whether or not image capturing corresponding to all the illumination units has been completed. When the CPU 21 determines that the image capturing corresponding to all the illumination units has not been completed (No in step S34), the process returns to step S32. Then, the light source control unit 31 performs the lighting driving on the illumination unit that undergoes the lighting driving next again, and the image capturing of the specimen 61 by the spectral camera device 1 is repeated under control of the image capturing control unit 32. As a result, each deflection angle spectral information corresponding to each illumination unit is stored in the HDD 24.

Then, when the image capturing corresponding to all the illumination units is determined to have been completed in step S34 (Yes in step S34), the process proceeds to step S35, and then the information correcting unit 35 corrects each deflection angle spectral information stored in the RAM 23 using the correction information of the image clarity and the orange peel stored in the HDD 24. In step S36, the measurement value calculating unit 36 calculates the measurement values of the image clarity and the orange peel using the corrected deflection angle spectral information as will be described later and stores the calculated measurement values in the storage unit such as the HDD 24, and then the process of the flowchart of FIG. 21 ends.

Next, a specific calculation operation of each evaluation item in the measurement value calculating unit 36 will be described. In the specimen measuring device according to the embodiment, light is emitted to the specimen from a plurality of illumination units installed at different angles with a previously calculated range. Then, an image of reflected light from the specimen is captured through the 2D spectral camera device 1 capable of acquiring the spectral information by one shot, and variable angle spectral information is obtained using a change in the optical geometrical condition of the illumination direction and the image capturing direction between pixels of the captured 2D image in the X axis direction and the Y axis direction.

The specimen measuring device according to the embodiment regards an in-plane as a uniform specimen. The measurement value calculating unit 36 calculates the deflection angle color measurement information and the BRDF information using the deflection angle spectral information in an angle range determined as a measurement range as follows.

Deflection Angle Spectral Information

The deflection angle spectral information is a deflection angle spectral reflection characteristic at a certain point x (i, j, θ, λ) on a specimen surface and stored in the storage unit such as the HDD 24 as information of each wavelength by the spectral camera device 1 as described above. "i" indicates a coordinate on the light receiving element on the X axis, "j" indicates a coordinate on the light receiving element on the Y axis, "θ" indicates an aspecular angle, and "λ" indicates a spectrally separated wavelength.

Deflection Angle Color Measurement Information

When the deflection angle color measurement information is calculated, the measurement value calculating unit 36 calculates the tristimulus values X, Y, and Z using the deflection angle spectral information as defined in a Commission Internationale de l'Eclairage (CIE). Then, conversion into a L*a*b* color system is performed by performing an operation illustrated in FIG. 22 using the tristimulus values X, Y, and Z, and the conversion result is used as the deflection angle color measurement information. Alternatively, the measurement value calculating unit 36 converts the tristimulus values X, Y, and Z into those of an L*u*v* color system by performing an operation illustrated in FIG. 23, and uses the conversion result as the deflection angle color measurement information.

BRDF Information

Figure 24:
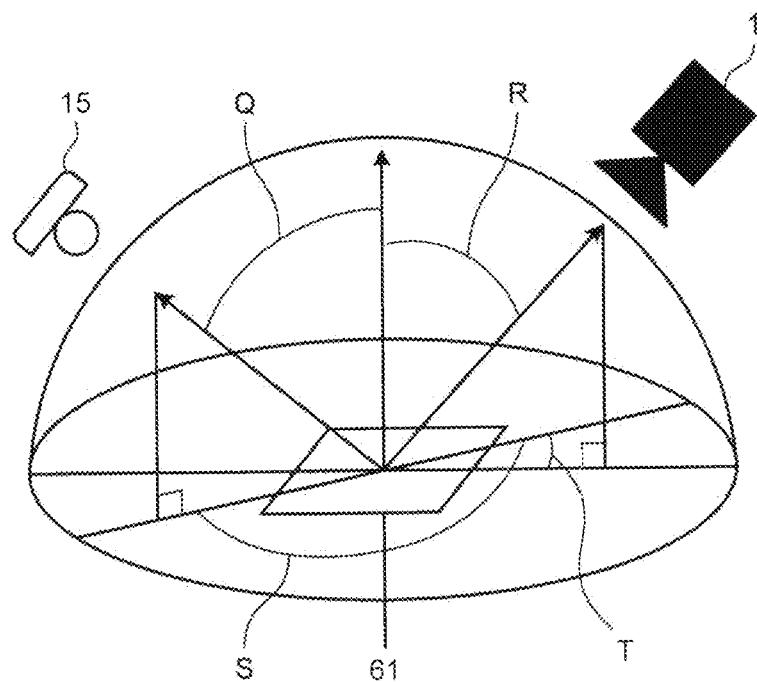
FIG. 24 is a diagram for describing an angle used for a definition of BRDF information.

In FIG. 24, a BRDF at a certain point x (i, j) on the surface of the specimen 61 is defined to depend on two directions of incidence and reflection and be proportional to a ratio of strength of reflected light in the image capturing direction (θr, φr) of the spectral camera device 1 to strength of incident light in a direction (θi, φi) of an illumination 15. An angle Q illustrated in FIG. 24 is θi, an angle R is φi, an angle S is θr, and an angle T is φr. A BRDF is defined for every three channels of red (R), green (G), and blue (B). Since the four angles Q, R, S, and T are commonly used as a parameter as in the following Formula (7), the measurement value calculating unit 36 calculates the BRDF information through an operation of the following Formula (7).

$$f_{BDRF}(X, \theta 1, \varphi i, \theta r, \varphi r,) \quad (7)$$

Acquisition of Texture Parameter

Further, the measurement value calculating unit 36 calculates a measurement value on the texture such as the glittering feeling, the graininess, the gloss, the haze, the image clarity, and the orange peel as follows.

Glittering Feeling

The spectral camera device 1 has an optical configuration in which the resolution for the specimen 61 is 10 μm to 100 μm per pixel. Further, the spectral camera device 1 captures an image of the specimen 61, for example, in the dynamic range of 18 or more bits using the high dynamic range technique.

The measurement value calculating unit 36 calculates a strength histogram for each illumination angle and each spectral wavelength, and calculates a glittering area, glittering strength, and glittering variance of each angle and wavelength. Specifically, for example, the measurement value calculating unit 36 calculates a strength histogram for each range of an angle 10°±2.5° at a wavelength of 555 nm, and calculates a strength histogram of a certain number or more of pixels. In this example, the strength histogram is calculated at intervals of 10°, but the strength histogram may be calculated at a different aspecular angle such as intervals of 5°, for example.

Figure 25:
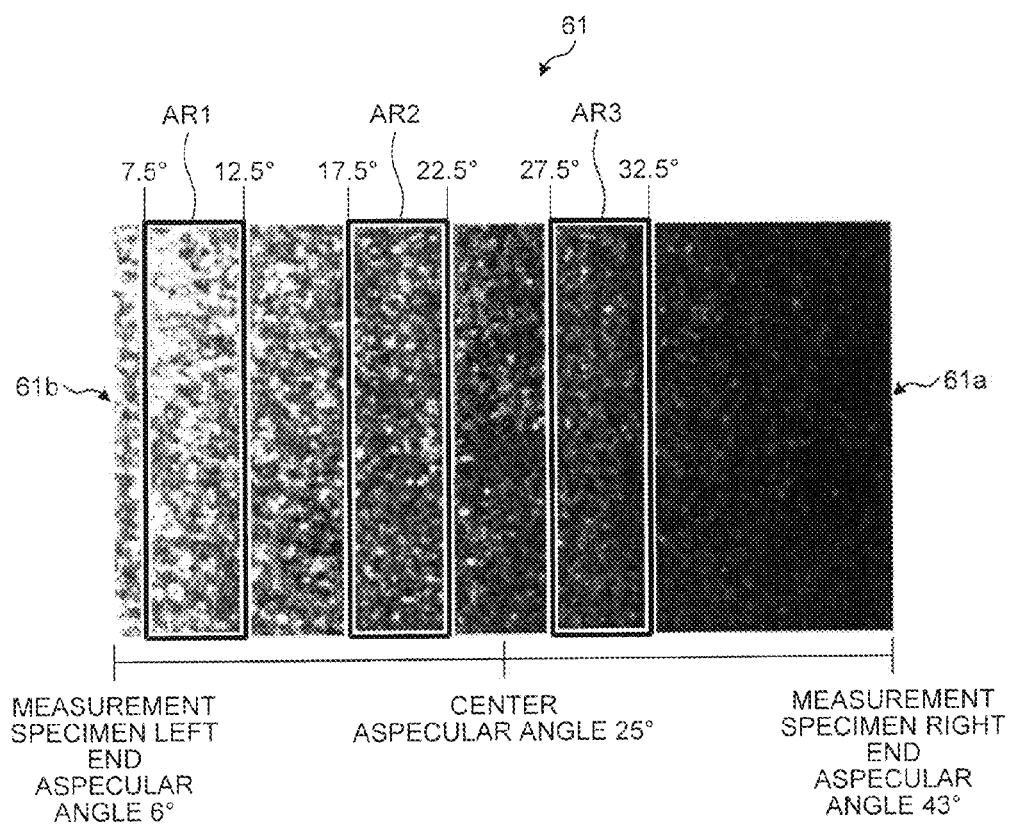
FIG. 25 is a diagram illustrating regions in which strength histograms of aspecular angles 10°, 20°, and 30° are calculated.
Figure 26:
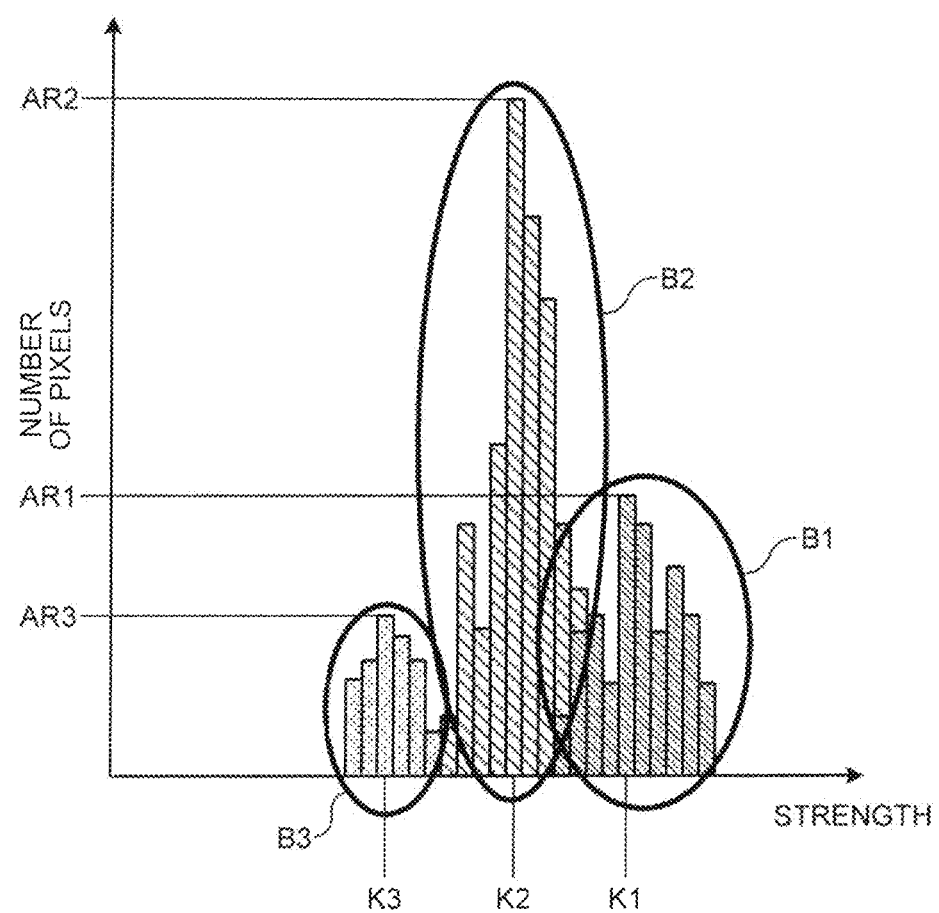
FIG. 26 is a diagram illustrating strength histograms of aspecular angles 10°, 20°, and 30°.

FIG. 25 illustrates regions for calculating strength histograms of aspecular angles 10°, 20°, and 30°. FIG. 26 illustrates the strength histograms of the aspecular angles 10°, 20°, and 30°. As illustrated in FIG. 25, the number of pixels at a peak at the aspecular angle 10° is assumed to be a "glittering area AR1," the number of pixels at a peak at the aspecular angle 20° is assumed to be a "glittering area AR2," and the number of pixels at a peak at the aspecular angle 30° is assumed to be a "glittering area AR3." Further, in FIG. 26, glittering strength at a peak at the aspecular angle 10° is assumed to be "glittering strength K1," glittering strength at a peak at the aspecular angle 20° is assumed to be "glittering strength K2," and glittering strength at a peak at the aspecular angle 30° is assumed to be "glittering strength K3." Furthermore, glittering variance of the histogram at the aspecular angle 10° is assumed to be "glittering variance B1," glittering variance of the histogram at the aspecular angle 20° is assumed to be "glittering variance B2," and glittering variance of the histogram at the aspecular angle 30° is assumed to be "glittering variance B3."

In this case, a glittering feeling parameter S(θ) at an angle θ can be indicated by three parameters of "S_area (θ)," "S_strength (θ)," and "S_variance (θ)," for example. The parameter of "S_area (θ)" is indicated by the glittering area (the number of pixels at the peak) AR1, the glittering area AR2, and the glittering area AR3. The parameter of "S_strength (θ)" is indicated by the glittering strength K1, the glittering strength K2, and the glittering strength K3 at the peak. The parameter of "S_variance (θ)" is indicated by the glittering variance B1, the glittering variance B2, and the glittering variance B3.

Figure 27A:
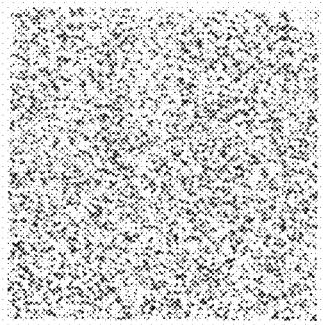
FIGS. 27A and 27B are diagrams illustrating images of a specimen of a metallic paint having fine particles and a strength histogram.
Figure 27B:
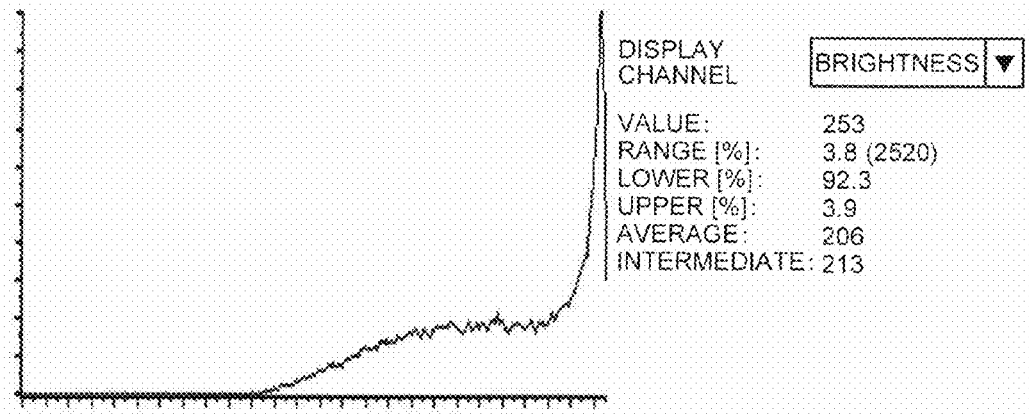
Figure 28A:
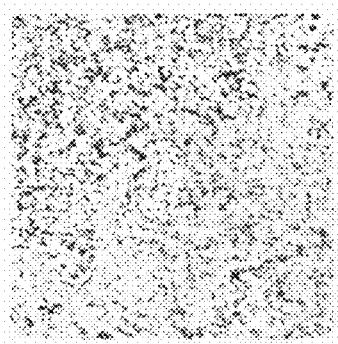
FIGS. 28A and 28B are diagrams illustrating images of a specimen of a metallic paint having coarse particles and a strength histogram.
Figure 28B:
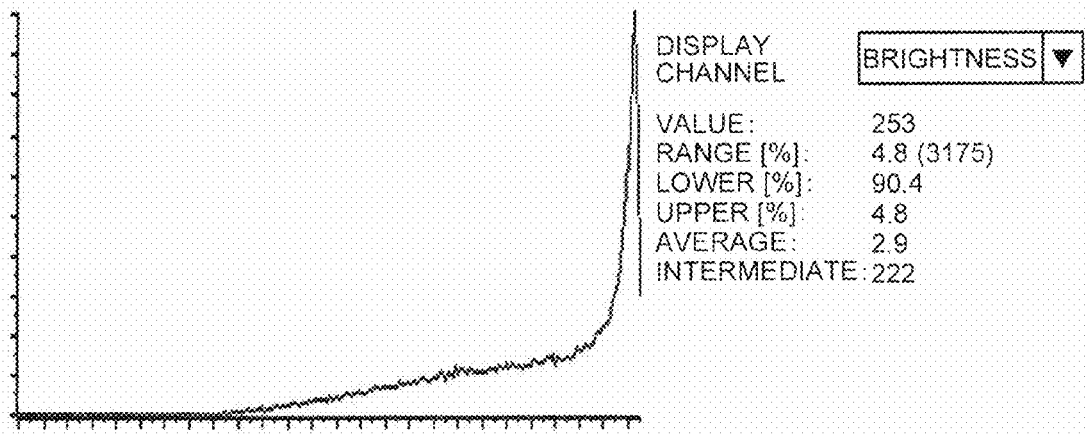
Figure 29A:
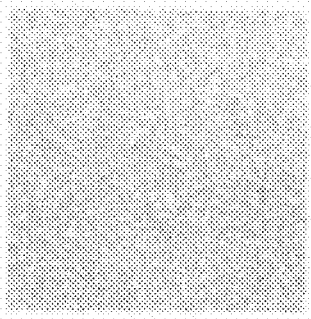
FIGS. 29A and 29B are diagrams illustrating images of a specimen of a pearlescent paint and a strength histogram.
Figure 29B:
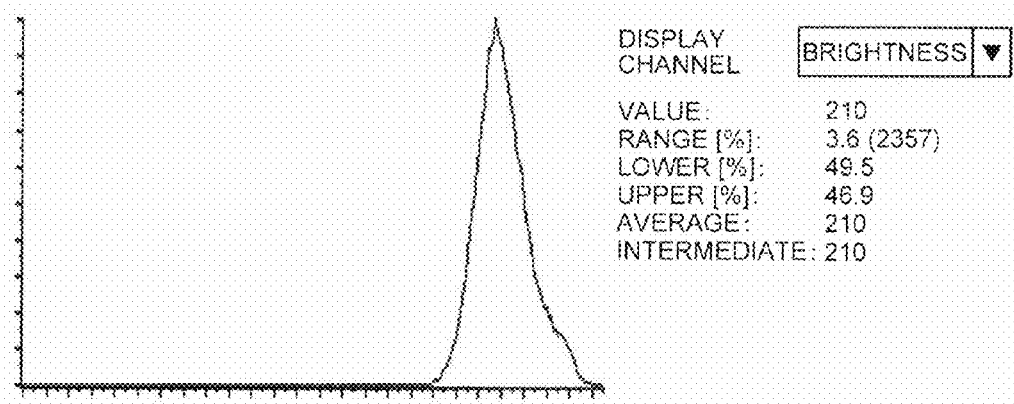

For example, a drawing labeled as (a) of FIG. 27 illustrates an image of a specimen of a metallic paint having fine particles, and a drawing labeled as (b) of FIG. 27 illustrates a strength histogram of a specimen of a metallic paint having fine particles. Further, a drawing labeled as (a) of FIG. 28 illustrates an image of a specimen of a metallic paint having coarse particles, and a drawing labeled as (b) of FIG. 28 illustrates a strength histogram of a specimen of a metallic paint having coarse particles. Furthermore, a drawing labeled as (a) of FIG. 29 illustrates an image of a specimen of a pearlescent paint, and a drawing labeled as (b) of FIG. 29 illustrates a strength histogram of a specimen of a pearlescent paint. FIGS. 27 to 29 illustrate the images and the strength histograms when an image of the specimen is captured in the vertical direction (see FIG. 17). The information processing device 4 illustrated in FIG. 1 causes the image of the specimen captured by the spectral camera device 1 and the calculated strength histogram to be displayed on the monitor device 5.

Graininess

The spectral camera device 1 has an optical configuration in which the resolution for the specimen 61 is 10 μm to 100 μm per pixel. Further, the spectral camera device 1 captures an image of the specimen 61, for example, in the dynamic range of 18 or more bits using the high dynamic range technique.

The measurement value calculating unit 36 reconstructs an image using only pixels determined to be diffusion light other than regular-reflected light of an illumination of a particle image of each illumination angle. In other words, when the description proceeds with the example illustrated in the strength histogram of FIG. 26, the measurement value calculating unit 36 reconstructs an image using only pixels except for the "glittering area AR2" and the "glittering area AR3" of the number of pixels at the peak.

Then, the measurement value calculating unit 36 calculates a variance value of a bright portion and a dark portion from the reconstructed image, and uses the calculated variance value as a measurement value of the graininess. The regular-reflected light is often regarded to be a noise, and the graininess is likely to be inaccurately calculated. However, it is possible to digitize the graininess accurately by performing the reconstruction of the image and the calculation of the variance value using only the pixels corresponding to the diffusion light other than the regular-reflected light. Further, when the variance value is small, it indicates that the particles of the paint are uniformly dispersed to the paint surface, and when the variance value is large, it indicates that the particles of the paint are sparsely dispersed to the paint surface. The digitization of the uniformity may be performed using an entropy of an image or may be performed by Fourier analysis.

Gloss

When the measurement value of the gloss is calculated, the measurement value calculating unit 36 uses the spectral strength information of 555 nm serving as human visibility for the pixel in which an image of specular reflected light is captured. Further, the measurement value calculating unit 36 calculates the measurement value of the gloss by performing an operation of the following Formula (8) according to Japanese Industrial Standards (JIS) Z8741-1997 Specular Glossiness Methods of Measurement.

$$Gs(\theta)=\varphi s/\varphi os * Gos(\theta) \qquad (8)$$

In Formula (8), "φs" indicates specular reflected light flux from a specimen surface for a specified incidence angle θ. "φos" indicates specular reflected light flux from a standard surface for a specified incidence angle θ. "Gos (θ)" indicates glossiness (%) of a used standard surface. The standard black glass or the standard mirror may be used as the standard surface.

Further, the measurement value calculating unit 36 calculates a flop index from information of the L*a*b* color system obtained by converting the tristimulus values X, Y, and Z, and calculates a flop characteristic (a degree of change in brightness). The flop Index refers to a relative change in the value of the information of the L*a*b* color system of each angle and brightness seen between and a high light and a shade.

The measurement value calculating unit 36 uses the following Formula (9) developed by DuPont as the flop index calculation formula.

$$\text{Flop Index}=2.69*(L*15-L*110)^{1.11}/(L*45)^{0.85} \qquad (9)$$

Further, a difference between a high light (15°) and a shade (110°) may be simply used as the flop Index without performing normalization at 45°.

Haze

The measurement value calculating unit 36 performs, for example, an operation of an "ASTM E-430 Test Method B" illustrated in FIG. 30 based on the spectral strength information of 555 nm serving as the human visibility for the specimen surface deviated from the regular-reflected light and the regular-reflected light by 1.9° to 3°, and calculates a measurement value of the haze. An example of FIG. 30 is an example of specular reflected light of 20°, and it can be extended according to an angle. For example, the example of FIG. 16 is an example of specular reflected light of 45°.

Then, when the measurement values of the image clarity and the orange peel are calculated, an image of slit light 80 of a certain short wavelength projected onto the specimen from a projector 1 is captured through the spectral camera device 1 as illustrated in FIG. 31. The measurement value calculating unit 36 performs, for example, an operation of an ASTM D5767-95 Test Method B expressed by the following Formula (10) using the spectral strength information of approximately 555 nm serving as the human visibility, and calculates the measurement values of the image clarity and the orange peel.

$$C=((M-m)/(M+m))\times 100 \qquad (10)$$

Figure 32A:
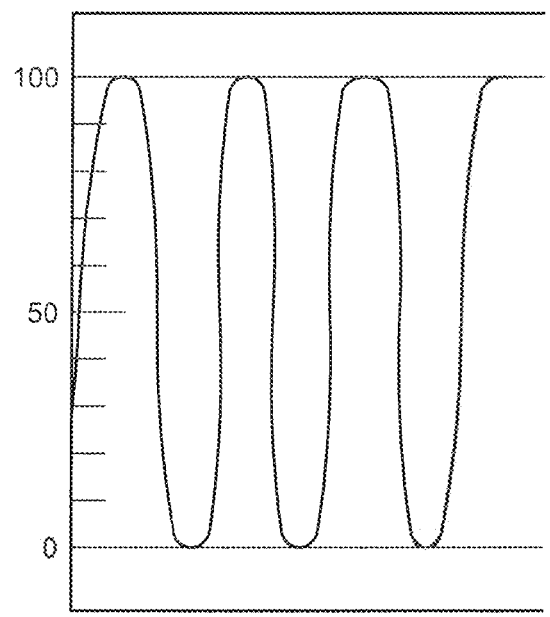
FIGS. 32A and 32B are diagrams for describing operational expressions for calculating measurement values of image clarity and orange peel.
Figure 32B:
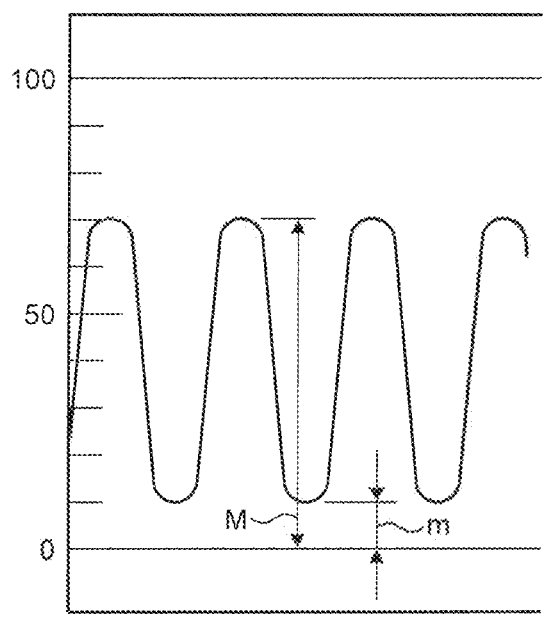
Figure 33:
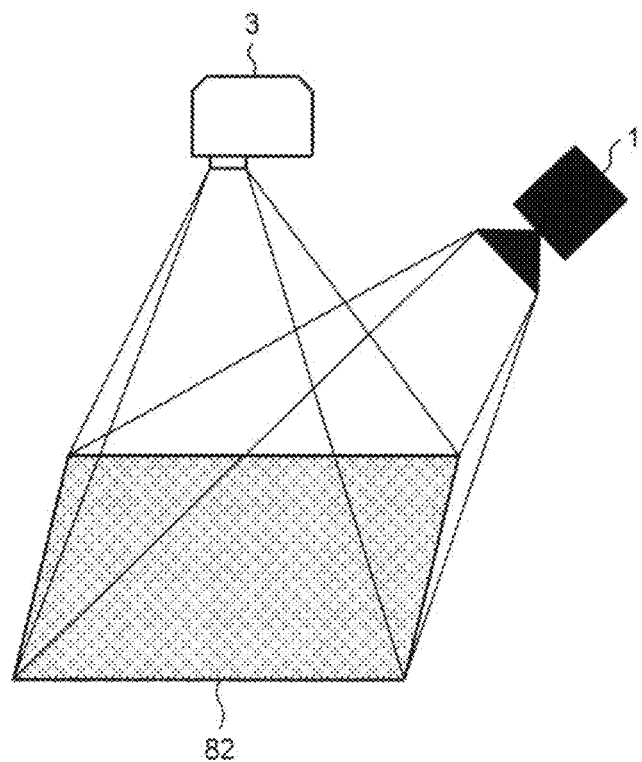
FIG. 33 is a diagram for describing a white noise projected by a specimen measuring device according to a second embodiment.

In Formula (10), "C" indicates the measurement value of the image clarity, "M" indicates a maximum value of the spectral strength information, and "m" indicates a minimum value of the spectral strength information. Drawings labeled as (a) and (b) of FIG. 32 illustrate an example of a spectral strength information waveform.

Orange Peel

When the measurement value of the orange peel is calculated, the slit light 80 is projected from the projector 3 and an image thereof is captured through the spectral camera device 1 as illustrated in FIG. 31, but when the orange peel is measured, slit light of a certain long wavelength is projected and an image thereof is captured. The measurement value calculating unit 36 calculates the measurement value of the orange peel using the spectral strength information of approximately 555 nm serving as the human visibility, for example, using Formula (10). For the orange peel, it is possible to evaluate comprehensive concave-convex characteristics having a longer period than the image clarity using the slit light 80 having a long period.

Further, the information processing device 4 illustrated in FIG. 1 causes the measurement values of the deflection angle spectral information, the deflection angle color measurement information, the BRDF information, the glittering feeling, the graininess, the gloss, the haze, the image clarity, and the orange peel which are calculated as described above to be displayed on the monitor device 5. The user can comprehensively evaluate the specimen based on the displayed measurement values.

As can be understood from the above description, the specimen measuring device according to the first embodiment irradiates the specimen 61 with the illumination at a plurality of angles installed within a range designated by the calculation formula, and captures an image of reflected light thereof through the 2D spectral camera device 1 capable of acquiring the spectral information by one shot. Further, the deflection angle spectral information is obtained using a change in the optical geometrical condition of the illumination direction and the image capturing direction between pixels in the X axis direction and the Y axis direction in the 2D image of the specimen 61. Further, an in-plane is regarded as a uniform specimen, and the deflection angle spectral information, the deflection angle color measurement information, and the BRDF information in the angle range determined as the measurement range are obtained.

Further, for the texture of the specimen 61, the digitized measurement information is calculated as follows. In other words, the glittering feeling is calculated as follows. An image of the specimen is captured in the dynamic range of 18 or more bits using the high dynamic range technique through the spectral camera device 1 having a resolution of 10 μm to 100 μm per pixel. The brightness histogram is calculated for each illumination angle and each spectral wavelength, and the glittering area and the glittering strength of each angle and wavelength are calculated.

The graininess is calculated as follows. The image of the specimen is reconstructed using only the pixels determined to be the diffusion light other than the regular-reflected light of the illumination of the particle image using the spectral camera device 1 having a resolution of 10 μm to 100 μm per pixel, and the uniformity of the bright/dark area is digitized from the image as the graininess. The uniformity may be obtained using the entropy or variance of the image or may be obtained by Fourier analysis.

The gloss is calculated as follows. For a pixel in which an image of the regular-reflected light is captured, the digitization is performed using spectral information of approximately 555 nm serving as human visibility and a correction result on the standard glass plate.

The haze (turbidity (opacity)) is calculated as follows. For the specimen surface deviated from the regular-reflected light and the regular-reflected light by 1.9° to 3°, the digitization is performed using the spectral information of approximately 555 nm serving as human visibility and a correction result on the standard glass plate.

The image clarity is calculated as follows. An image of the slit light (having a short wavelength) projected from the projector 3 is captured through the spectral camera device 1, and the digitization is performed using the spectral information of approximately 555 nm serving as human visibility and a correction result on the standard glass plate.

The orange peel is calculated as follows. An image of the slit light (having a long wavelength) projected from the projector 3 is captured through the spectral camera device 1, and the digitization is performed using the spectral information of approximately 555 nm serving as human visibility and a correction result on the standard glass plate.

The specimen measuring device according to the first embodiment can calculate the measurement value of the respective evaluation items such as the deflection angle spectral information, the deflection angle color information, the BRDF information, the glittering feeling, the graininess, the gloss, the haze, the image clarity, and the orange peel of a paint including a glittering material that looks a different color according to an observation angle such as a pearlescent color or a metallic color. Thus, it is possible to perform a comprehensive quantitative evaluation of a paint including a glittering material that looks a different color according to an observation angle at a time.

Second Embodiment

Next, a specimen measuring device according to a second embodiment will be described. The specimen measuring device according to the first embodiment emits and captures an image of slit light 81 when the image clarity is measured.

On the other hand, the specimen measuring device according to the second embodiment controls the projector 3 such that the pattern projection control unit 33 projects a 2D white noise 82 including a spatial frequency of up to an image capturing limit spatial frequency of the spectral camera device 1 onto the specimen as illustrated in FIG. 31 when a timing to measure the image clarity comes. Further, as described above, the light source control unit 31 performs the lighting driving on the illumination units sequentially, and the image capturing control unit 32 performs the image capturing control on the spectral camera device 1 to capture an image of the white noise 82.

The white noise has the same strength at all frequencies when a Fourier transform is performed, so that it is transformed into a power spectrum. The measurement value calculating unit 36 calculates 2D spatial frequency characteristics obtained by performing the Fourier transform on a captured image of the white noise as the measurement value of the image clarity. The 2D spatial frequency characteristics obtained by performing the Fourier transform on the captured image of the white noise become a spatial frequency response of an image to spatial frequencies of all incident images. Thus, even when the white noise is projected instead of the slit light 80, it is possible not only to calculate the image clarity but also to obtain the same effect as in the first embodiment.

Third Embodiment

Next, a specimen measuring device according to a third embodiment will be described. The specimen measuring device according to the third embodiment can perform measurement that is not influenced by the shape of the measurement target surface by correcting the optical geometrical condition of the 3D shape of each position of the specimen surface.

Figure 34:
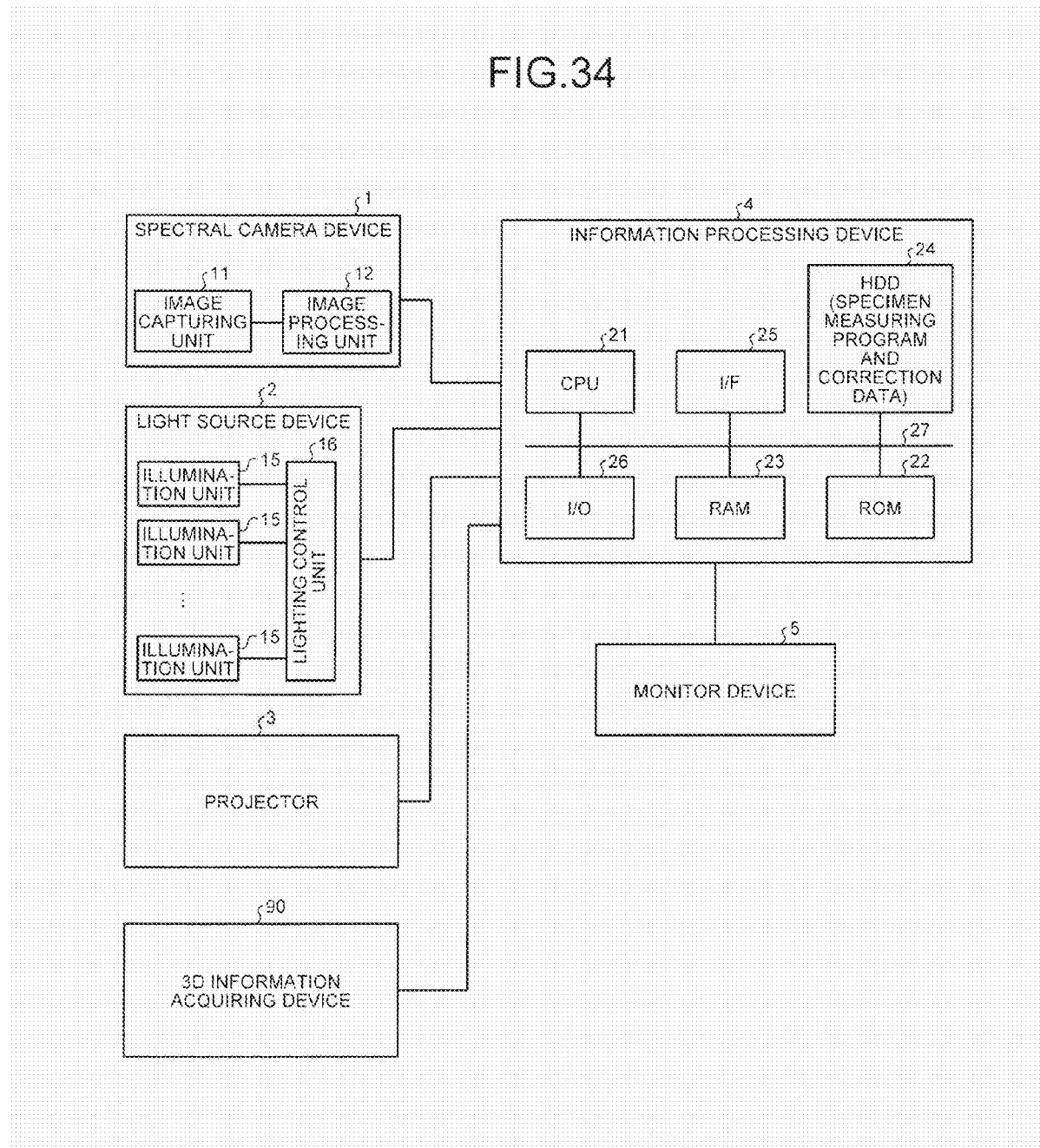
FIG. 34 is a block diagram of a specimen measuring device according to a third embodiment.

Specifically, the specimen measuring device according to the third embodiment acquires the slit light projected from the projector 3 or the 3D shape of each position of the specimen surface through a 3D information acquiring device 90 illustrated in FIG. 34. The measurement value calculating unit 36 calculates a normal line direction of each position of the specimen from the acquired 3D shape of each position of the specimen surface. Then, the measurement value calculating unit 36 corrects the calculated normal line direction of each position of the specimen and a regular reflection direction of light from the illumination unit based on a positional relation among the spectral camera device 1, each illumination unit, and the specimen, and re-calculates the aspecular angle. As a result, it is possible to correct the optical geometrical condition of the 3D shape of each position of the specimen surface.

When the deflection angle characteristics of the specimen are measured, even when the specimen is inclined from the horizontal direction by 1°, a deviation occurs even in the deflection angle characteristics. However, the specimen measuring device according to the third embodiment can correct the deviation in the deflection angle characteristics inclined by 1° based on the normal line direction of the specimen surface and a geometric arrangement thereof and perform the calculation. For this reason, by calculating the normal line direction from the 3D shape of each position of the specimen, correcting, the regular reflection direction of the illumination, and calculating the aspecular angle again, it is possible to perform the measurement that is not influenced by the shape of the measurement target surface, obtain the more accurate measurement value of each evaluation item, and obtain the same effect as in the above embodiments.

Fourth Embodiment

Next, a specimen measuring device according to a fourth embodiment will be described. In the above embodiments, for example, the spectral camera device 1 performs the image capturing by one shot while performing the lighting control on the illumination units 15f to 15h illustrated in FIG. 17 one by one.

Figure 35:
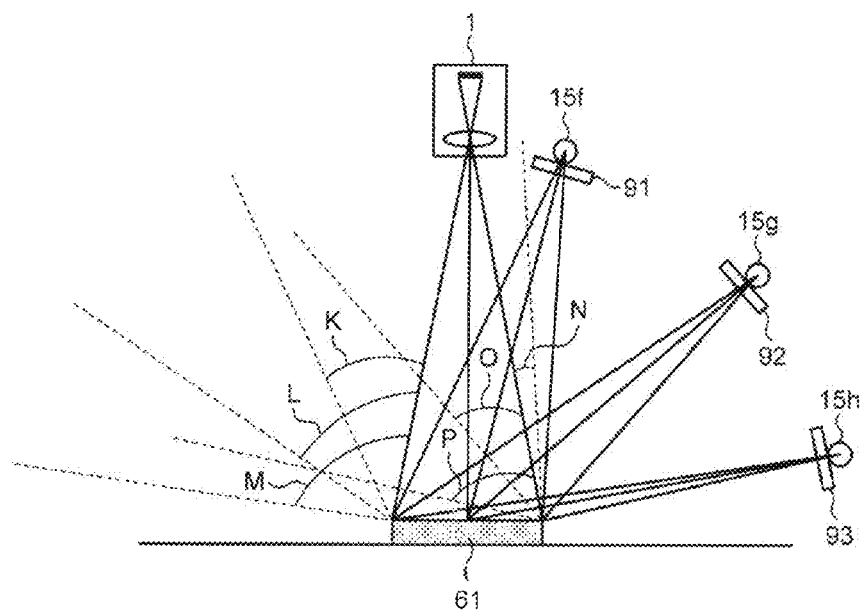
FIG. 35 is a diagram illustrating positions of filters installed in a specimen measuring device according to a fourth embodiment.
Figure 36:
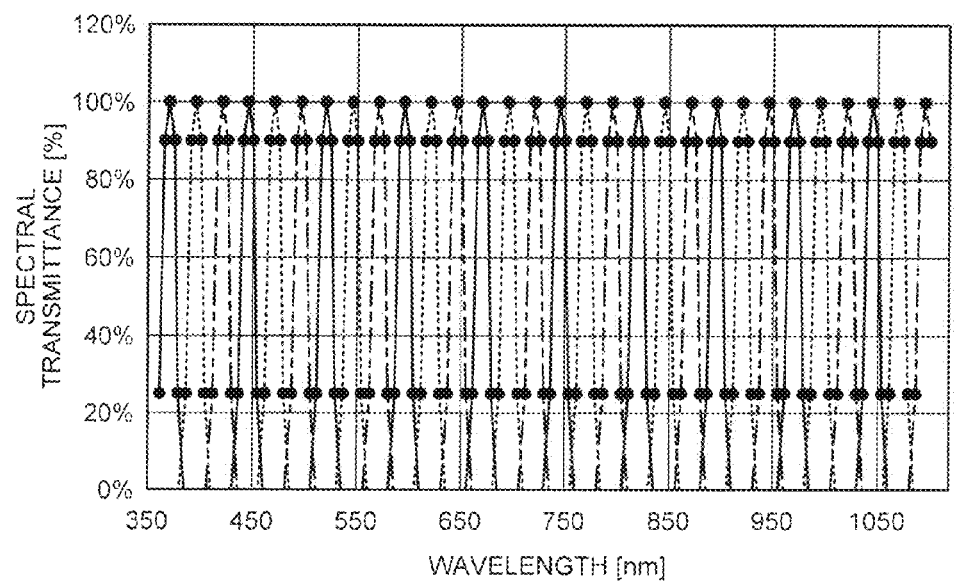
FIG. 36 is a diagram for describing spectral transmittance characteristics of filters installed in the specimen measuring device according to the fourth embodiment.

On the other hand, in the specimen measuring device according to the fourth embodiment, filters 91, 92, and 93 having different spectral transmittance characteristics are installed in front of the illumination units 15f to 15h as illustrated in FIG. 35. The illumination units 15f to 15h may be coated with paints having different spectral transmittance characteristics. The filters 91, 92, and 93 have spectral transmittance characteristics illustrated in FIG. 36. In FIG. 36, for example, a graph of a solid line illustrates spectral transmittance characteristics of the filter 91, a graph of a dotted line illustrates spectral transmittance characteristics of the filter 92, and a graph of an alternate long and short dash line illustrates spectral transmittance characteristics of the filter 93. As can be seen from FIG. 36, wavelengths of light to be transmitted in the filters 91, 92, and 93 are deviated by a certain degree.

The light source control unit 31 performs the lighting control on all the illumination units 15f to 15h simultaneously. Further, when "the lighting control is performed simultaneously," the lighting control may be performed at a time in a state in which lighting timings of the illumination units 15f to 15h are set to the same timing, or the light control may be performed on one or more of the illumination units 15f to 15h, and then the lighting control may be finally performed on all the illumination units 15f to 15h simultaneously. In other words, it is desirable to perform the lighting control on the illumination units 15f to 15h so that there is a period of time in which the illumination units 15f to 15h are turned on simultaneously.

The image capturing control unit 33 performs the image capturing control on the spectral camera device 1 so that the single image capturing operation is performed while the lighting control is being performed on all the illumination units 15f to 15h simultaneously. As a result, it is possible to acquire the deflection angle spectral information and the deflection angle color measurement information corresponding to the respective illumination units 15f to 15h at a time through one shot. Accordingly, it is possible to reduce a period of time to measure the specimen, and it is possible to obtain the same effects as in the above embodiments.

According to an embodiment, an effect that the quality of various paints can be comprehensively quantified is obtained.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A specimen measuring device, comprising:
   a light source device configured to irradiate a specimen surface of a specimen with illumination light from multiple illumination units at a plurality of illumination angles;
   a spectral camera device arranged above the specimen surface, the spectral camera configured to spectrally separate reflected light from the specimen surface and to generate two-dimensional (2D) spectral information through a single image capturing operation; and
   processing circuitry configured to calculate deflection angle spectral information of the specimen surface used to measure a measurement value of a certain evaluation item of the specimen using a change in an optical geometrical condition of an illumination direction and an image capturing direction between pixels in an X axis direction and a Y axis direction of the spectral information, wherein
   the light source device changes at least one of a light quantity and an exposure time at a time of image capturing, and
   the spectral camera device synthesizes a plurality of pieces of 2D spectral information acquired according to a change in a light quantity, an exposure time at a time of image capturing, or a light quantity and an exposure time at a time of image capturing by the light source device, and generates the 2D spectral information having an enlarged dynamic range.

2. The specimen measuring device according to claim 1, wherein
   the optical geometrical condition is at least one of a measurement range of the specimen surface, an angle of view of the spectral camera device, a distance between the specimen surface and one of the illumination units, a distance between the spectral camera device and the one of the illumination units, and the illumination angle of one of the illumination units, and
   the one of the illumination units and the spectral camera device are arranged such that a deflection angle range to be measured is continuously acquired in the optical geometrical condition.

3. The specimen measuring device according to claim 1, wherein the processing circuitry calculates a brightness histogram for each illumination angle and each spectral wavelength using the 2D spectral information acquired by the spectral camera device, and calculates a glittering area and glittering strength of each illumination angle and each spectral wavelength.

4. The specimen measuring device according to claim 1, wherein the processing circuitry determines a rank of a diffusion light reflection angle excluding a regular reflection angle based on the 2D spectral information acquired by the spectral camera device, reconstructs an image using only pixels determined to be diffusion light other than regular-reflected light of an illumination of a particle image of each illumination angle, and calculates uniformity of an area of a bright portion and a dark portion as a graininess based on the reconstructed image using an entropy, variance or Fourier analysis of an image.

5. The specimen measuring device according to claim 1, wherein the processing circuitry calculates a gloss value from a regular reflection angle, and calculates a haze value from the regular reflection angle and an adjacent angle using the deflection angle spectral information.

6. The specimen measuring device according to claim 1, further comprising:
   a projector that projects slit light of a certain pattern in an image capturing range of the spectral camera device, wherein
   the processing circuitry measures measurement values of an image clarity and an orange peel of the specimen using the deflection angle spectral information generated by capturing an image of the slit light through the spectral camera device.

7. The specimen measuring device according to claim 6, wherein
   the projector projects an image of a white noise in the image capturing rage of the spectral camera device, and the processing circuitry calculates the measurement value of the image clarity of the specimen using the deflection angle spectral information obtained by capturing an image of the white noise through the spectral camera device.

8. The specimen measuring device according to claim 1, wherein the processing circuitry is further configured to
acquire three-dimensional (3D) information shape information of the specimen surface of the specimen,
calculate a normal line direction of each position of the specimen surface using the acquired 3D shape information of the specimen surface, and
correct the deflection angle spectral information acquired by the spectral camera device using the calculated normal line direction.

9. The specimen measuring device according to claim 1, wherein the processing circuitry calculates measurement values of deflection angle color information, BRDF information, a glittering feeling, a graininess, a gloss, a haze, image clarity, and orange peel using the deflection angle spectral information.

10. The specimen measuring device according to claim 1, wherein
the spectral camera device is a multi-band camera that that includes a main lens, a group of spectral filters, and a micro lens, and acquires spectral information according to number of the spectral filters, or a hyper spectral camera that includes one or more sets of filters and diffraction gratings or prisms, and
the spectral camera device acquires the 2D spectral information in synchronization with irradiation of illumination light of each illumination angle of the illumination unit through a single image capturing operation.

11. The specimen measuring device according to claim 10, wherein the multi-band camera includes the group of spectral filters inserted into the main lens and a micro lens array inserted between the main lens and a light sensor, and acquires the spectral information according to the number of the spectral filters through each micro lens of the micro lens array.

12. The specimen measuring device according to claim 11, wherein the multi-band camera acquires the spectral information according to the number of the spectral filters as the group of the spectral filters is installed between the micro lens array and the light sensor.

13. The specimen measuring device according to claim 1, wherein the spectral camera device has an optical configuration in which each pixel is 10 μm to 1.011 μm of the specimen.

14. A non-transitory computer-readable medium storing executable instructions that, when executed by a computer, cause the computer to:
control a light source device to irradiate a specimen surface of a specimen with illumination light from multiple illumination units at a plurality of illumination angles;
control the light source device to change at least one of a light quantity and an exposure time at a time of image capturing;
control a spectral camera device arranged above the specimen surface to spectrally separate reflected light from the specimen surface and to generate two-dimensional (2D) spectral information through a single image capturing operation; and
calculate deflection angle spectral information of the specimen surface used to measure a measurement value of a certain evaluation item of the specimen using a change in an optical geometrical condition of an illumination direction and an image capturing direction between pixels in an X axis direction and a Y axis direction of the spectral information, wherein
the spectral camera device is controlled to synthesize a plurality of pieces of 2D spectral information acquired according to a change in a light quantity, an exposure time at a time of image capturing, or a light quantity and an exposure time at a time of image capturing by the light source device, and to generate the 2D spectral information having an enlarged dynamic range.

* * * * *